(12) United States Patent
Moschel et al.

(10) Patent No.: US 6,303,604 B1
(45) Date of Patent: Oct. 16, 2001

(54) PHARMACEUTICAL COMPOSITION COMPRISING 2,4-DIAMINO-6-BENZYLOXY-S-TRIAZINE AND INACTIVATION OF $O^6$-ALKYLGUANINE-DNA-ALKYLTRANSFERASE

(75) Inventors: Robert C. Moschel, Frederick, MD (US); Anthony E. Pegg, Hershey, PA (US); M. Eileen Dolan, Oak Park, IL (US); Mi-Young Chae, Frederick, MD (US)

(73) Assignees: The United States of America as represented by the Department of Health and Human Services, Washington, DC (US); The Penn State Research Foundation, University Park, PA (US); Arch Development Corporation, Chicago, IL (US)

( * ) Notice: Subject to any disclaimer, the term of this patent is extended or adjusted under 35 U.S.C. 154(b) by 0 days.

(21) Appl. No.: 09/590,187

(22) Filed: Jun. 9, 2000

Related U.S. Application Data

(62) Division of application No. 09/318,238, filed on May 25, 1999, now Pat. No. 6,172,070, which is a division of application No. 08/927,846, filed on Sep. 11, 1997, now Pat. No. 5,916,894, which is a division of application No. 08/661,923, filed on Jun. 11, 1996, now Pat. No. 5,753,668, which is a division of application No. 08/283,953, filed on Aug. 1, 1994, now Pat. No. 5,525,606.

(51) Int. Cl.[7] .................................................. A61K 31/53
(52) U.S. Cl. ........................................... 514/245; 435/184
(58) Field of Search .............................. 513/245; 435/184

(56) References Cited

U.S. PATENT DOCUMENTS

| | | | |
|---|---|---|---|
| 4,199,574 | 4/1980 | Schaeffer | 424/200 |
| 4,495,190 | 1/1985 | Hagberg et al. | 514/262 |
| 4,751,221 | 6/1988 | Watanabe et al. | 514/46 |
| 4,801,710 | 1/1989 | MacCoss et al. | 544/244 |
| 4,965,270 | 10/1990 | Harnden et al. | 514/262 |
| 5,075,445 | 12/1991 | Jarvest et al. | 544/276 |
| 5,091,430 | 2/1992 | Moschel et al. | 514/262 |
| 5,352,669 | 10/1994 | Moschel et al. . | |
| 5,358,952 | 10/1994 | Moschel et al. . | |
| 5,364,904 | 11/1994 | Farmer et al. . | |
| 5,525,606 | 6/1996 | Moschel et al. | 514/262 |
| 5,691,307 | 11/1997 | Moschel et al. . | |
| 5,731,304 | 3/1998 | Baer et al. . | |
| 5,753,668 | 5/1998 | Moschel et al. . | |
| 5,916,894 | 6/1999 | Moschel et al. | 514/262 |
| 5,929,046 | 7/1999 | McMurray et al. | 514/45 |
| 5,958,932 | 9/1999 | Moschel et al. | 514/262 |

FOREIGN PATENT DOCUMENTS

| | | |
|---|---|---|
| 0 184 473 | 6/1986 | (EP) . |
| 0335355 | 10/1989 | (EP) . |
| WO 91/13898 | 9/1991 | (WO) . |
| WO 94/29312 | 12/1994 | (WO) . |
| WO 96/04281 | 2/1996 | (WO) . |
| WO 97/20843 | 6/1997 | (WO) . |

OTHER PUBLICATIONS

Robert T. Dorr and William L. Fritz, "Cancer Chemotherapy Handbook—Regulatory and Medicolegal Aspects of Investigational Cancer Chemotherapy" Elsevier Science Publishing, NY, NY, pp. 715–742 (1980).

Bisacchi et al., "Synthesis and Antiviral Activity of Enantiomeric Forms of Cyclobutyl Nucleoside Analogues", J. Med. Chem., vol. 34, No. 4, pp. 1415–1421 (1991).

Bowles et al., "Synthesis and Antitumor Activity of 9–(Tetrahydro–2–furyl)purine Analogs of Biologically Important Deoxynucleosides", *J. Med. Chem.*, vol. 6, pp. 471–480 (Mar. 11, 1963).

Brix et al., "Androgen–Linked Alkylating Agents: Biological Activity in Methylnitrosourea–Induced Rat Mammary Carcinoma", J. Cancer Research Clinical Oncology, vol. 116, pp. 538–549 (1990).

John A. Carbon, "Synthesis and Reactions of 5–Bromomethyl– and 5–Chloromethyluracil", vol. 25, Mar. 25, pp. 1731–1734 (1960).

Dolan et al., "Depletion of $O^6$–Alkylguanine–DNA Alkyltransferase Activity in Mammalian Tissues and Human Tumor Xenografts in Nude Mice by Treatment with $O^6$–Methylguanine", *Cancer Chemotherapy and Pharmacology*, vol. 25, pp. 103–108 (1989).

Harnden et al., "Synthesis and Antiviral Activity of 9–[4–Hydroxy–3–(hydroxymethyl)but–L–yl]purines", J. Med, Chem. vol. 30, pp. 1636–1642 (1987).

Harnden et al., "Prodrugs of the Selective Antiherpesvirus Agent 9–[4–Hydroxy–3–(hydroxymethyl)but–L–y]guanine (BRL 39123) with Improved Gastrointestinal Absorption Properties", J. Med. Chem., vol. 32, pp. 1738–1743 (1989).

Himmeslbach et al., "The p–Nitrophenylethyl (NPE) Group—A Versatile New Blocking Group for Phosphate and Aglycone Protection in Nucleosides and Nucleotides", Tetrahedron, vol. 40, No. 1, pp. 59–72 (1984).

(List continued on next page.)

*Primary Examiner*—Frederick Krass
(74) *Attorney, Agent, or Firm*—Leydig, Voit & Mayer, Ltd.

(57) ABSTRACT

The present invention provides 8-substituted $O^6$-benzylguanine, 4(6)-substituted 2-amino-5-nitro-6(4)-benzyloxypyrimidine, and 4(6)-substituted 2-amino-5-nitroso-6(4)-benzyloxypyrimidine derivatives which have been found to be effective AGT inactivators, as well as pharmaceutical compositions comprising such derivatives along with a pharmaceutically acceptable carrier. The present invention further provides a method of enhancing the chemotherapeutic treatment of tumor cells in a mammal with an antineoplastic alkylating agent which causes cytotoxic lesions at the $O^6$-position of quanine, by administering to a mammal an effective amount of one of the aforesaid derivatives, 2,4-diamino-6-benzyloxy-s-triazine, 5-substituted 2,4-diamino-6-benzyloxypyrimidines, or 8-aza-$O^6$-benzylguanine, and administering to the mammal an effective amount of an antineoplastic alkylating agent which causes cytotoxic lesions at the $O^6$-position of guanine.

3 Claims, No Drawings

OTHER PUBLICATIONS

Holmes et al., "Rearrangement of Cinnamyl Groups from $O^6$ to C–8 in the Guanine Series", J. Org. Chem., vol. 43, No. 3, pp. 516–518 (1978).

Jacobs et al., "Synthesis of SQ–32,829, a New Nucleoside Antiviral Agent", Tetrahedron Letters, vol. 30, No. 50, pp. 6955–6958 (1989).

Karkas et al., "Enzymatic Phosphorylation of the Antiherpetic Agent 9–[(2,3–Dihydroxy–L–propoxy)methyl]guanine", J. Med. Chem. vol. 29, No. 5, pp. 842–848 (1986).

Kim et al., "Acyclic Purine Phosphonate Analogues as Antiviral Agents. Synthesis and Structure–Activity Relationships", J. Med. Chem., vol. 33, No. 4, pp. 1207–1213 (1990).

Kjellberg et al., "Regioselective Alkylation of 6–(β–Methoxyethoxy) Guanine to Give the 9–Alkylguanine Derivative", Tetrahedron Letters, vol. 27, No. 7, pp. 877–880 (1986).

Kusmierek et al. "Synthesis of $N^2$,3–Ethenodeoxyguanosine, $N^2$,3–Ethenodeoxyguanosine 5' –Phosphate, and $N^2$,3–Ethenodeoxyguanosine 5'–Triphosphate. Stability of the Glycosyl Bond in the Monomer and in Poly(dG, dG–dC)", Chem. Res. Toxicol., vol. 2, pp. 230–233 (1989).

House, "Modem Synthetic Reactions", Second Edition, W. A. Benjamin, pp. 536–541 (1972).

House, "Modem Synthetic Reactions", Second Edition, W. A. Benjamin, pp. 602–603 (1972).

Leonard et al., "Intramolecular Mechanism of the Allylic Rearragement from $O^6$ to C–8 in the Guanine Series, Double Labeling Experiments", J. A. Chem. Soc., vol. 96, pp. 5894–5903 (1974).

March, Advanced Org. Chem., Third Edition, John Wiley and Sons, pp. 358–359, 574–575,802–803, and 982–985 (1985).

MacCoss et al., "Synthesis of the Chiral Acyclonucleoside Antiherpetic Agent (S)–9–(2,3–Dihydroxyl–1–Propoxymethyl)Guanine", Tetrahedron Letters, vol. 26, No. 15, pp. 1815–1818 (1985).

Milne et al., "Synthesis and Antitumor Activity of Δ– and E–2'–Deoxy–6–selenoguanosine and Certain Related Derivatives", Journal of Medicinal Chemistry, vol. 17, No. 3, pp. 253–286 (1974).

Moschel et al., "Substituent–Induced Effects on the Stability of Benzylated Guanosines: Model Systems for the Factors Influencing the Stability of Carcinogen–Modified Nucleic Acids", J. Org. Chem., vol. 49, No.2, pp. 363–372 (1984).

Dolan et al., "Comparison of the Inactivation of Mammalian and Bacterial $O^6$–alkylguanine–DNA Alkyltransferases by $O^6$–Benzylguanine and $O^6$–Methylguanine", *Carcinogenesis,* vol. 12, No. 12, pp. 2305–2309 (1991).

Winograd et al., "Human Tumor Xenografts in the Nude Mouse and their Value as Test Models in Anticancer Drug Development (Review)", In Vivo, vol. 1, pp. 1–14 (1987).

J. Gerald Wilson, "Synthetic Approaches to a Carboranyl Thiouracil", Pigment Cell Research 2, pp. 297–303 (1989).

Raymond G. Wallace, "Hydroxylamine–0–Sulfonic Acid—a Versatile Synthetic Reagent" Aldrichimica Acta, vol. 13, No. 1, pp. 3–11 (1980).

Gerson et al., Synergistic Efficacy of $O^6$–Benzylguanine and 1,3–Bis(2–Chloroethyl)–1–Nitrosourea (BCNU) in a Human Colon Cancer Xenograft Completely Resistant to BCNU Alone, Biochemical Pharmacology, vol. 45, No. 2, pp. 483–491 (1993).

Ramzaera et al., "Alkalation of 6–Methylthio– and 6–Benzyloxyguanine under Phase–Transfer Conditions", Synthetic Communications, vol. 19, No. 18, pp. 3121–3128 (1989).

Skinner et al., "Potential Anticancer Agents. XXVIII. Synthesis of 5–(Chloromethyl)uracil", Organic Chem., vol. 25, pp. 149–151 (1960).

Pegg et al., "Use of Antibodies to Human $O^6$–Alkylgvuanine–DNA Alkytransferase to Study the Content of this Protein in Cells Treated with $O^{6-}$Benzylguanine or N–Methyl–N'–Nitro–N–Nitrosoguanidine", Carcinogenesis, vol. 12, No. 9, pp. 1679–1683 (1991).

Slusarchyk et al., "Synthesis of SQ–33–054, a Novel Cyclobutane Nucleoside with Potent Antiviral Activity", Tetrahedron Letters, vol. 30, No. 47, pp. 6453–6456 (1989).

Stein et al., "Inhibition of Human Purine Nucleoside Phosphorylase by Acyclic Nucleosides and Nucleotides", Biochemical Pharmacology, vol. 36, No.8, pp. 1237–1244 (1989).

Trichtinger et al., "Synthesis of $O^6$–p–Nitrophenylethyl Guanosine and 2'–Deoxyguanosine Derivatives", Tetrahedron Letters, vol. 24, No. 7, pp. 711–714 (1983).

Vemishetti et al., "Synthesis of Chiral 1',2'–Seco–Nucleosides of Guanine and Uracil", Nucleosides & Nucleotides, vol. 8, No. 2, pp. 201–211 (1989).

Vemishetti et al., "The Preparation of 2'–Deoxy–2'–fluoro–1',2'–seconucleosides as Potential Antiviral Agents", J. Med. Chem. vol. 33, pp. 681–685 (1990).

Dolan et al., "Effect of $O^6$–Alkylguanine Pretreatment on the Sensitivity of Human Colon Tumor Cells to the Cytotoxic Effects of Chloroethylating Agents", *Cancer Research,* vol. 46, pp. 4500–4504 (1986).

Fischer et al., "The Cancer Chemotherapy Handbook", Third Edition, YearBook Medical Publishers, Inc., Chapter 1 pp. 4–9, 60–61, 164–165, 171 (Copyright 1989).

Hannah et al., "Carba–acyclonucleoside Antiherpetic Agents", Merck Sharp & Dohme Research Laboratories, vol. 26, pp. 1261–1271 (Sep.–Oct. 1989).

Pauly et al., "Synthesis and Properties of H–ras DNA Sequences Containing $O^6$–Substituted 2'–Deoxyguanosine Residues at the First, Second, or Both Positions of Codon 12", Chem. Res. in Taxicol. vol. 1, No. 6, pp. 292–297 (1989).

Ford et al., "A Simple Method for Predicting Hydration Energies of Organic Cations Derived from Protonation or Alkylation of Neutral Oxygen and Nitrogen Bases", J. Org. Chem. vol. 48, No. 13, pp. 2226–2233 (1983).

Fondy et al., "Haloacentamido Analogues of 2–Amino–2–deoxy–D–glucose and 2–Amino–2–deoxy–D–galactose. Syntheses and Effects on the Friend Murine Erythroleukemia", Journal of Medicinal Chemistry, vol. 21, No. 12, pp. 1222–1225 (1978).

Folkman et al., "A New One–Step Method for the Preparation of 3',5'–Bisphosphates of Acid–Labile Deoxynucleosides", Chem. Res. Toxicol. vol. 3, pp. 536–539 (1990).

Robert W. Murray, "Dioxiranes", Chem. Rev., vol. 89, pp. 1187–1201 (1989).

Pansare et al. "Synthesis of N–Protected Δ–Amino Acids from N–(Benxyloxycarbonyl)–L–Serine via its E–Lactone: $N^{66}$–(Bensyloxycarbonyl)–E–(Pyrazol–L–YL)–L–Alanine", Organic Syntheses, vol. 70, No. 1, pp. 1–9 (1992).

Pansare et al. :Synthesis of N–tert–Butoxycarbonyl–L–Serine E–Lactone and the p–Toluenesulfonic Acid Salt of (S)–3–Amino–2–Oxetanone, Organic Syntheses, vol. 70, pp. 10–17 (1992).

Pauly et al., "A Sectored Colony Assay for Monitoring Mutagenesis by Specific Carcinogen–DNA Adducts in *Escherichia Coli*", Biochemistry, vol. 30. No. 50, 11700–11706 (1991).

Anthony E. Pegg, "Mammalian $O^6$–Alkylguanine–DNA Alkyltransferase: Regulation and Importance in Response to Alkylating Carcinogenic and Therapeutic Agents", Cancer Research, vol. 50, pp. 6119–6129 (Oct. 1, 1990).

Moschel et al., "Substituent–Induced Effects on the Stability of Benxylated Guanosines: Model Systems for the Factors Influencing the Stability of Carcinogen–Modified Nucleic Acids", The Journal of Organic Chemistry, vol. 49, pp. 363–372 (1984).

"Chemical Abstracts", vol. 101, No. 25, pp. 1 and 765–766 (Dec. 17, 1984).

"Harrison's Principles of Inernal Medicine", Tenth Edition, McGraw–Hill Book Company, pp. 757–775 (1984).

Frihart et al., "Allylic Rearrangement from $O^6$ to C–8 in the Guanine Series", Journal of the American Chemical Society, vol. 95, No. 21, pp. 7174–7175 (1973).

Zahler et al., "Purinyl– and Pyromidinylcyclobutanes and their Use as Antiviral Agents", Chem. Abs., vol. 113: 152981k, (1990).

American Chemical Society, Chemical Abstracts Service Registry Handbook, No. Section 1965–1971, 1126R, col. 3, Registry No. 30360–74–8 (published mid 1970's).

Beecham Group, "Preparation of Guanine Derivatives and Their Use in Antiviral Preparations," 28–Heterocyles, 103:123509a (1985).

Biasacchi et al., Preparation of [1E–(1Δ,2E,3Δ)]–2–amino–9[2,3–bis(hydroxymethyl)cyclobutyl]–6H–purin–6–one Chem. Abs., 115:159683q (1970).

*Chemical Abstract* 72: 100650 (1970).

*Chemical Abstract* 107: 194511 (1987).

*Chemical Abstract* 112: 216531 (1989).

Green et al., "Preparation of Purine Acyclonucleoside Intermediates," Chem. Abs., 115:2899t (1991).

Hagberg et al., "Guanine Derivatives", 33–Carbohydrates, 97:182809d (1982).

Hannah et al., "Substituted Butylguanines and Their Utilization in Antiviral Composition," 26–Niomolrvulrd, 104–68682 (1986).

Hannah et al., "Carba–acylonucleoside Antiherpetic Agents", J. Heterocyclic Chem., vol. 26, pp. 1261–1271 (1989).

Harrison's Principles of Internal Medicine, $10^{th}$ ed., pp. 751, 758, 766–775 (1983).

MacCoss et al., "Regioselective Synthesis of 9–Substituted Purine Acyclonucleoside Derivatives", 33–Carbohydrates, 105:11538f (1986).

Mansuri et al., "Preparation of 4–phosphoromethoxycyclopent(en)–L–ylpurines and –pyrimidines as Virucides, Bactericides, and Neoplasm Inhibitors", Chem. Abs., 113:152983n (1990).

Moschel et al., "Reactivity Effects on Site Selectivity in Nucleoside Aralkylation: A Model for the Factors Influencing the Sites of Carcinogen–Nucleic Acid Interactions", 33–Carbohydrates, 107:115902r (1989).

Murray, "Dioxiranes", Chem. Rev., vol. 89, No. 5, pp. 1187–1201 (1989).

Rideout et al., "Preparation of (3'–azido–2',3'–dideozy) Purine Nucleosides as Medical Antivirals", Chem. Abs., 116:84108r (1992).

Robins et al., "Purine Nucleosides. XXIV. A New Method for the Synthesis of Guanine Nucleosides. Preparation of 2'–deoxy–Δ– and –E–guanosines and the Corresponding $N^2$–methl derivatives" 34–Synthesis of Amino Acids, Peptides, and Proteins, 71:39386w (1969).

Schaffer et al., "Substituted Purine Derivates", Chem Abs., 84:180300p (1976).

Schaffer et al., "Compositions for Treating Viral Infections and Guanine Acyclic Nucleosides", Chem. Abs., 93:186414m (1980).

Slusarchyk et al., "Preparation of [bis(hydroxymethyl)cyclobutyl]Purines and –pyrimidines as Antiviral Agents", Chem. Abs., 113:40344y (1990).

Tisdale et al., "Preparation of 2'–deoxy–2'–fluororibonucleosides as Medicinal Virucides", Chem. Abs., 115:230514t (1991).

Tolman et al., "4–(Guanin–9–yl)butanals and Antiviral Compositions Containing Them", Chem. Abs., 105:11484)r (1986).

Tolman et al., "9–[2–(Hydroxymethyl)cycloalkylmethyl] guainines as Antiviral Agents and Their Preparation", 26–Biomolecules, 110:212501d (1989).

Tondeur et al. "Fast Atom Bombardment and Collisional Activation Mass Spectrometry as Probes for the Identification of Positional Isomers in a Series of Benzylated Guanosines", Chem. Abs., 104:199241y (1986).

Wallace, Raymond, "Hydroxylamine–0–sulfonic Acid—A Versatile Synthetic Reagent", Aldrichimia Acta, vol. 13, pp. 3–11 (1980).

Webb et al., "Antiviral Phosphonomethoxyalkylpurines and – pyrimidines and Their Preparation", 26–Biomolecules, 109:190136 (1988).

Webb et al., "Preparation of [(purin–9–ylalkoxy)methyl] phosphonic Acids as Antiviral Agents", Chem. Abs., 111:39105y (1989).

Wilson, "Synthetic Approaches to a Carboranyl Thiouracil", Pigment Cell Research, vol. 2, pp 297–303 (1989).

Yu et al., "Preparation of Chiral 2–(phosphonomethyoxy)propylguanines as Antiviral Agents", Chem. Abs., 116:41987j (1992).

Zahler et al., "Preparation of Purinyl– and Pyrimidinylcyclobutanes as Antiviral Agents", Chem. Abs., 113:1588265f (1990).

Zahler et al., "Preparation of Virucidal Purinyl– and Pyrimidinyl–tetrahydrofurans" 33–Carbohydrates 114:122985t (1991).

Zahler et al., "Preparation of 4,5–bis(hydroxymethyl)tetrahydrofuran–3–y purines and Pyrimidines as Virucides", 33–Carbohydrates, 116:84113p (1991).

Costanzi, "DTIC (NSC–45388) Studies in the Southwest Oncology Group", Cancer Treatment Reports, vol. 60, No. 2, pp. 189–192 (1976).

Newlands et al., "Phase I Trial of Temozolomide (CCRG 81045: M&B 39831: NDSC 362856)", Br. J. Cancer, vol. 65, pp. 287–291 (1992).

Stevens et al., "Antitumor Activity and Pharmacokinetics in Mice of 8–Carbamoyl–3–methyl–imidazo[5,1–d]–1,2,3, 5–tetrazin–4(3H)–one (CCRG 81045; M & B 39831), a Novel Drug with Potential as an Alternative to Dacarbazine", Cancer Research, vol. 47, pp. 5846–5852 (1987).

Stevens et al., "From Triazines and Triazenes to Temozolomide", Eur. J. Cancer, vol. 29A, No. 7, pp. 1045–1047 (1993).

Tsang et al., "Comparison of the Cytotoxicity in vitro of Temozolomide and Dacarbazine, Prodrugs of 3–methyl–(triazen–L–yl)imidazole–4–carboxamide", Cancer Chemother. Pharmacol., vol. 27, pp. 342–346 (1991).

Beaman et al., in Zorbvack and Tipson, (Synthetic Procedures in Nucleic Acid Chemistry, vol. 1, pp 41–43 (John Wiley & Sons, New York, NY 1968.

Boon et al., *J. Chem. Soc.*, pp. 96–102 (1951).

Chae et al., *J. Med. Chem.*, vol. 37, No. 3, pp. 342–347 (1947).

Chae et al., *J. Med. Chem.*, vol. 38, No. 2., pp. 359–365 (1995).

Crone et al., *Cancer Res.*, vol. 53, pp. 4750–4753 (1993).

Daves, Jr. et al., *J. Am. Chem. Soc.*, vol. 82, pp. 2633–2640 (1960).

Dalia et al., *Heterocycles,* vol. 20, pp. 1805–1909 (1983).

Dolan et al., *Proc. Natl. Acad. Sci. U.S.A.,* vol. 87, pp. 5368–5372 (1990).

Dolan et al., *Cancer Commun.* vol. 2, pp. 371–377 (1990).

Dolan et al., *Cancer Res.,* vol. 51, pp. 3367–3372 (1991).

Dolan et al., *Biochem. Pharmacol.,* vol. 46, pp. 285–290 (1993).

Dolan et al., *Cancer Chem. Pharmacol.,* vol. 32, pp. 221–225 (1993).

Felker et al., *Cancer Chem. Pharmacol.,* vol. 32, pp. 471–476 (1993).

Friedman et al., *J. Natl. Cancer Inst.,* vol. 84, pp. 1926–1931 (1992).

Gerster et al., *J. Am. Chem. Soc.,* vol. 87, pp. 3752–3759 (1965).

Jones et al., *J. Am. Chem. Soc.,* vol. 82, pp. 3773–37779 (1960).

Kosary et al., *Acta Pharm. Hung.,* vol. 49, pp. 241–247 (1989).

Mitchell et al., *Cancer Res.,* vol. 52, pp. 1171–1175 (1992).

Moschel et al., *J. Med. Cham.,* vol. 35, No. 23, pp. 4486–4491 (1992).

Moschel et al., *J. Org. Chem.,* vol. 51, pp. 4180–4185 (1986).

O'Brien et al., *J. Med. Chem.,* vol. 9, pp. 573–575 (1966).

Pfleiderer et al., *Chem. Ber.,* vol. 94, pp. 12–18 (1961).

Pfleiderer et al., *Liebigs Ann. Chem.,* vol. 726, pp. 201–215 (1969).

Phillips et al., *J. Org. Chem.,* vol. 28, pp. 1488–1490 (1963).

Ram et al., *Chem. Abstr.,* vol. 101, No. 25, 2304661 (1984).

Robbins et al., *J. Org. Chem.,* vol. 34, No. 7, pp. 2160–2163 (1969).

Shealey et al., *J. Org. Chem.,* vol. 27, pp. 4518–4523 (1962).

Wakabayashi et al., *Nippon Dojo–Hiryyogaku Zasshi,* vol. 41, pp. 193–200 (1970) (Abstract CA73:108869m).

Wasserman et al., *Cancer,* vol. 36, pp. 1258–1268 (1975).

PHARMACEUTICAL COMPOSITION COMPRISING 2,4-DIAMINO-6-BENZYLOXY-S-TRIAZINE AND INACTIVATION OF $O^6$-ALKYLGUANINE-DNA-ALKYLTRANSFERASE

This application is a divisional of U.S. Ser. No. 09/318,238, filed May 25, 1999 and now U.S. Pat. No. 6,172,070, which is a divisional of U.S. Ser. No. 08/927,846, filed Sep. 11, 1997 and now U.S. Pat. No. 5,916,894, which is a divisional of U.S. Ser. No. 08/661,923, filed Jun. 11, 1996 and now U.S. Pat. No. 5,753,668, which is a divisional of U.S. Ser. No. 08/283,953, filed Aug. 1, 1994 and now U.S. Pat. No. 5,525,606.

TECHNICAL FIELD OF THE INVENTION

The present invention relates to substituted $O^6$-benzylguanines and 6(4-benzyloxypyrimidines, pharmaceutical compositions comprising such compounds, and methods of using such compounds. The subject compounds are particularly useful in inactivating the human DNA repair protein $O^6$-alkylguanine-DNA alkyltransferase.

BACKGROUND OF THE INVENTION

The inactivation of the human DNA repair protein $O^6$-alkylguanine-DNA alkyltransferase (AGT) by $O^6$-benzylguanine leads to a dramatic enhancement in the cytotoxic response of human tumor cells and tumor xenografts to chemotherapeutic drugs whose mechanism of action involves modification of DNA quanine residues at the $O^6$-position (Dolan et al., *Proc. Natl. Acad. Sci. U.S.A.*, 87, 5368–5372 (1990); Dolan et al., *Cancer Res.*, 51, 3367–3372 (1991); Dolan et al., *Cancer Commun.*, 2, 371–377 (1990); Mitchell et al., *Cancer Res.*, 52, 1171–1175 (1992); Friedman et al., *J. Natl. Cancer Inst.*, 84, 1926–1931 (1992); Felker et al., *Cancer Chem. Pharmacol.*, 32, 471–476 (1993); Dolan et al., *Cancer Chem. Pharmacol.*, 32, 221–225 (1993); Dolan et al., *Biochem. Pharmacol.*, 46, 285–290 (1993)). The AGT inactivating activity of a large number of $O^6$-benzylguanine analogs have been compared with the aim of obtaining information about the types of substituent groups and the sites at which they could be attached to $O^6$-benzylguanine without significantly lowering its AGT-inactivating activity (Moschel et al., *J. Med. Chem.*, 35, 4486–4491 (1992); Chae et al., *J. Med. Chem.*, 37, 342–347 (1994)). While these studies led to the production of a variety of analogs that were at potent or somewhat less potent than $O^6$-benzylguanine, none of the analogs were better than $O^6$-benzylguanine.

Thus, there remains a need for additional compounds which are capable of enhancing the chemotherapeutic treatment of tumor cells in a mammal with an antineoplastic alkylating agent which causes cytotoxic lesions at the $O^6$-position of guanine. The present invention provides such compounds and associated pharmaceutical compositions and treatment methods. These and other objects and advantages of the present invention, as well as additional inventive features, will be apparent from the description of the invention provided herein.

BRIEF SUMMARY OF THE INVENTION

The present invention provides 8-substituted $O^6$-benzylguanine derivatives and 4(6)-substituted 2-amino-5-nitro-6(4)-benzyloxypyrimidine and 2-amino-5-nitroso-6 (4)-benzyloxypyrimidine derivatives which have been found to be effective AGT inactivators, as well as pharmaceutical compositions comprising such derivatives along with a pharmaceutically acceptable carrier. The present invention further provides a method of enhancing the chemotherapeutic treatment of tumor cells in a mammal with an antineoplastic alkylating agent which causes cytotoxic lesions at the $O^6$-position of guanine, by administering to a mammal an effective amount of one of the aforesaid derivatives, 2,4-diamino-6-benzyloxy-s-triazine, 5-substituted 2,4-diamino-6-benzyloxypyrimidines, or 8-aza-$O^6$-benzylguanine, and administering to the mammal an effective amount of an antineoplastic alkylating agent which causes cytotoxic lesions at the $O^6$-position of guanine.

DESCRIPTION OF THE PREFERRED EMBODIMENTS

The present invention provides a compound of the formula (Formula I)

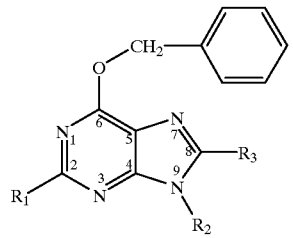

wherein $R_1$ is a substituent selected from the group consisting of amino, hydroxy, $C_1$–$C_4$ alkylamino, $C_1$–$C_4$ dialkylamino, and $C_1$–$C_4$ acylamino (although, as explained in further detail below, other substituents can be placed at this 2-position), $R_2$ is a substituent selected from the group consisting of hydrogen, $C_1$–$C_4$ alkyl, $C_1$–$C_4$ aminoalkyl, $C_1$–$C_4$ hydroxyalkyl, $C_1$–$C_4$ alkylaminoalkyl, $C_1$–$C_4$ dialylaminoalkyl, $C_1$–$C_4$ cyanoalkyl, $C_1$–$C_4$ carbamoylalkyl, $C_1$–$C_4$ pivaloylalkyl, $C_1$–$C_4$ carboalkoxyalkyl, ribose, 2'-deoxyribose, the conjugate acid form of a $C_1$–$C_4$ carboxyalkyl, and the carboxylate anion of a $C_1$–$C_4$ carboxyalkyl as the sodium salt (although, as explained in further detail below, other substituents can be placed at this $N^9$-position), and $R_3$ is a substituent selected from the group consisting of hydrogen, halo, $C_1$–$C_4$ alkyl, $C_1$–$C_4$ hydroxyalkyl, thiol, $C_1$–$C_4$ alkylthio, trifluoromethylthio, $C_1$–$C_4$ thioacyl, hydroxy, $C_1$–$C_4$ alkoxy, trifluoromethoxy, oxymethanesulfonyl, oxytrifluoromethanesulfonyl, $C_1$–$C_4$ oxyacyl, amino, $C_1$–$C_4$ aminoalkyl, $C_1$–$C_4$ alkylamino, $C_1$–$C_4$ dialkylamino, trifluoromethylamino, ditrifluoromethylamino, aminomethanesulfonyl, $C_1$–$C_4$ aminoacyl, aminotrifluoromethylcarbonyl, formylamino, nitro, nitroso, $C_1$–$C_4$ alkyldiazo, $C_5$–$C_6$ aryldiazo, trifluoromethyl, $C_1$–$C_4$ haloalkyl, $C_1$–$C_4$ cyanoalkyl, cyano, $C_1$–$C_4$ alkyoxycarbonyl, $C_1$–$C_4$ alkylcarbonyl, phenyl, phenylcarbonyl, $C_1$–$C_4$ acyl, formyl, $C_1$–$C_4$ alkoxymethyl, phenoxymethyl, $C_1$–$C_4$ vinyl, $C_1$–$C_4$ ethynyl, and $SO_nR'$ wherein n is 0, 1, 2, or 3 and R' is hydrogen, $C_1$–$C_4$ alkyl, amino, or phenyl, with the proviso that $R_1$ is not amino when both $R_2$ and $R_3$ are hydrogen. Of particular interest are those compounds wherein $R_1$ is amino, $R_2$ is hydrogen or $C_1$–$C_4$ alkyl (preferably methyl), and/or $R_3$ is amino, $C_1$–$C_4$ alkyl (preferably methyl), hydroxy, halo (preferably bromine), nitro, or trifluoromethyl. Also of particular interest are those compounds wherein $R_1$ is hydroxy, $C_1$–$C_4$ alkylamino (preferably methylamino), $C_1$–$C_4$ dialkylamino (preferably dimethylamino), or $C_1$–$C_4$ acylamino (preferably acylamino, i.e., $CH_3COHN$—), $R_2$ is hydrogen, and/or $R_3$ is hydrogen or hydroxy.

The present invention also provides a compound of the formula (Formula II)

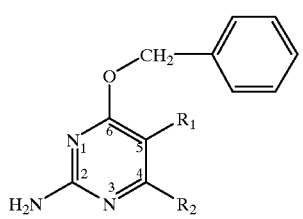

wherein $R_1$ is $NO_2$ or NO, and $R_2$ is a substituent selected from the group consisting of hydrogen, halo, $C_1$–$C_4$ alkyl, $C_1$–$C_4$ hydroxyalkyl, thiol, $C_1$–$C_4$ alkylthio, trifluoromethylthio, $C_1$–$C_4$ thioacyl, hydroxy, $C_1$–$C_4$ alkoxy, trifluoromethoxy, oxymethanesulfonyl, oxytrifluoromethanesulfonyl, $C_1$–$C_4$ oxyacyl, $C_1$–$C_4$ aminoalkyl, $C_1$–$C_4$ alkylamino, $C_1$–$C_4$ dialkylamino, trifluoromethylamino, ditrifluoromethylamino, aminomethanesulfonyl, $C_1$–$C_4$ aminoacyl, aminotrifluoromethylcarbonyl, formylamino, nitro, nitroso, $C_1$–$C_4$ alkyldiazo, $C_5$–$C_6$ aryldiazo, trifluoromethyl, halomethyl, $C_1$–$C_4$ haloalkyl, cyanomethyl, $C_1$–$C_4$ cyanoalkyl, cyano, $C_1$–$C_4$ alkyoxycarbonyl, $C_1$–$C_4$ alkylcarbonyl, phenyl, phenylcarbonyl, $C_1$–$C_4$ acyl, formyl, $C_1$–$C_4$ alkoxymethyl, phenoxymethyl, $C_1$–$C_4$ vinyl, $C_1$–$C_4$ ethynyl, and $SO_nR'$ wherein n is 0, 1, 2, or 3 and R' is hydrogen, $C_1$–$C_4$ alkyl, amino, or phenyl. Of particular interest are those compounds wherein $R_2$ is hydrogen or a $C_1$–$C_4$ alkyl, preferably methyl, particularly when $R_1$ is $NO_2$.

The present invention additionally provides treatment methods, which are generally administered via pharmaceutical compositions comprising one or more of the $O^6$-substituted compounds of the present invention. In particular, the present invention provides a method of enhancing the chemotherapeutic treatment of tumor cells in a mammal with an antineoplastic alkylating agent that causes cytotoxic lesions at the $O^6$-position of guanine, which method comprises administering to a mammal an effective amount of one or more of the aforedescribed present inventive compounds, and administering to the mammal an effective amount of an antineoplastic alkylating agent that causes cytotoxic lesions at the $O^6$-position of guanine. The present invention also includes the method of enhancing the chemotherapeutic treatment of tumor cells in a mammal with an antineoplastic alkylating agent that causes cytotoxic lesions at the $O^6$-position of guanine, which method comprises (i) administering to a mammal an effective amount of (a) a compound of the formula (Formula III)

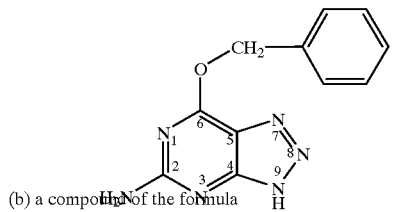

(b) a compound of the formula (Formula IV)

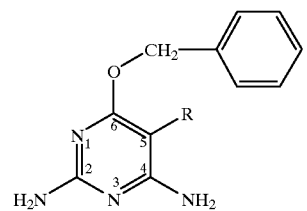

wherein R is a substituent selected from the group consisting of hydrogen, halo, $C_1$–$C_4$ alkyl, $C_1$–$C_4$ hydroxyalkyl, thiol, $C_1$–$C_4$ alkylthio, trifluoromethylthio, $C_1$–$C_4$ thioacyl, hydroxy, $C_1$–$C_4$ alkoxy, trifluoromethoxy, oxymethanesulfonyl, oxytrifluoromethanesulfonyl, $C_1$–$C_4$ oxyacyl, amino, $C_1$–$C_4$ aminoalkyl, $C_1$–$C_4$ alkylamino, $C_1$–$C_4$ dialkylamino, trifluoromethylamino, ditrifluoromethylamino, aminomethanesulfonyl, $C_1$–$C_4$ aminoacyl, aminotrifluormethylcarbonyl, formylamino, nitro, nitroso, $C_1$–$C_4$ alkyldiazo, $C_5$–$C_6$ aryldiazo, trifluoromethyl, halomethyl, $C_1$–$C_4$ haloalkyl, cyanomethyl, $C_1$–$C_4$ cyanoalkyl, cyano, $C_1$–$C_4$ alkoxycarbonyl, $C_1$–$C_4$ alkylcarbonyl, phenyl, phenylcarbonyl, $C_1$–$C_4$ acyl, formyl, $C_1$–$C_4$ alkoxymethyl, phenoxymethyl, $C_1$–$C_4$ vinyl, $C_1$–$C_4$ ethynyl, and $SO_nR'$ wherein n is 0, 1, 2, or 3 and R' is hydrogen, $C_1$–$C_4$ alkyl, amino, or phenyl, or (c) a compound of the formula (Formula V)

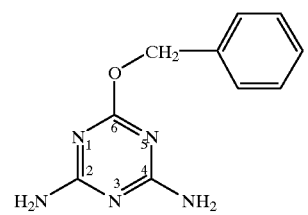

and (ii) administering to the mammal an effective amount of an antineoplastic alkylating agent which causes cytotoxic lesions at the $O^6$-position of guanine.

Various substitutions onto the present inventive compounds and those compounds useful in the context of the present inventive method are possible while retaining the effectiveness of those compounds. In particular, the $N^9$ position of the compounds of Formulas I and III, and the 2- and/or 4-positions of the compounds of Formulas I–V, can be substituted with a variety of substituents (which can be used instead of any existing substituents at those positions). Such substitutions include aryl, a substituted aryl wherein the aryl substituents are selected from the group consisting of $C_1$–$C_6$ alkyl, $C_1$–$C_6$ alkoxy, nitro, halo, a polycyclic aromatic alkyl containing 2–4 aromatic rings, $C_2$–$C_6$ alkenyl, $C_2$–$C_6$ alkynyl, $C_1$–$C_6$ haloalkyl, $C_1$–$C_6$ hydroxyalkyl, $C_1$–$C_6$ halohydroxy alkyl, acyloxy, an acyloxyalkyl wherein the alkyl is $C_1$–$C_6$, carboxy, the acid or salt form of carboxyalkyl wherein the alkyl is $C_1$–$C_6$, carbonyl, carbamoyl, a carbamoylalkyl wherein the alkyl is $C_1$–$C_6$, hydrazinocarbonyl, chlorocarbonyl, cyano, $C_2$–$C_9$ cyanoalkyl, C-formyl, a dialkoxymethyl wherein the alkoxy is $C_1$–$C_6$, C-acyl, an alkoxy hydroxyalkyl wherein the alkyl and the alkoxy are $C_1$–$C_6$, carboxymethyl thio, a carboalkoxy alkyl wherein the alkoxy and alkyl are $C_1$–$C_6$, a monoalkylamino hydroxylalkyl wherein the alkyl is $C_1$–$C_6$, a dialkylamino hydroxyalkyl wherein the alkyl is $C_1$–$C_6$, amino hydroxyalkyl wherein the alkyl is $C_1$–$C_6$, a peptide derived from the β-lactone of L-serine, or related amino acids, a monosaccharide selected from the group consisting of aldotetroses, aldopentoses and aldohexoses, a polysaccharide selected from the group consisting of sucrose, lactose, maltose and cellobiose, a nucleic acid segment, a steroid selected from the group consisting of testosterone, nortestosterone, and dihydrotestosterone, and $SO_nR'$ wherein n is 0, 1, 2, or 3 and R' is H, $C_1$–$C_6$ alkyl or aryl.

The benzene ring of the benzyl groups also may be substituted with one or more suitable substituents such as, for example, hydrogen, halo, nitro, nitroso, aryl, substituted aryl, aralkyl, substituted aralkyl, polycyclic aromatic arylalkyl, alkyl, cycloalkyl, alkenyl, alkynyl, trifluoromethyl, hydroxy, hydroxyalkyl, alkoxy, alkoxyalkyl, aryloxy, acyloxy, acyloxyalkyl, oxo, amino, monoalkylamino, dialkylamino, hydrazino, hydroxyamino, acylamino, ureido, thioureido, amidino, guanidino, carboxy, carboxyalkyl, alkoxycarbonyl, carbamoyl, hydrazinocarbonyl, chlorocarbonyl, cyano, cyanoalkyl, C-formyl, dialkoxymethyl, C-acyl, cyanato, isocyanato, thiocyanato, isothiocyanato, carboxymethylthio, aminoalkyl, alkylamino, aminocarboxyalkyl, peptides, carbohydrate, polysaccharide, steroid, heterocycle, aromatic heterocycle, nucleic acid derivative, and $SO_nR_1$ wherein n is 0, 1, 2, or 3, and $R_1$ is hydrogen, alkyl or aryl, The hydrocarbon substituents, such as alkyl, alkoxy, aminoalkyl, alkylamino, and the like, will typically be $C_1$–$C_6$, more typically $C_1$–$C_4$.

The range of substituents found useful with respect to the identified positions on the compounds of Formulas I–V are generally electron withdrawing, as noted in applicants' related U.S. patent application Ser. No. 07/875,438 now abandoned and hereinbelow. Further information regarding useful substituents for AGT depleting compounds of the present invention is also provided in applicants' other related U.S. Pat. Nos. 5,358,952, 5,091,430 and 5,352,669. Collectively, the compounds useful in the context of the present invention are referred to herein as $O^6$-substituted compounds.

Several 2- and/or 8-substituted 6-benzyloxypurines, substituted 6(4)-benzyloxypyrimidines, and a 6-benzyloxy-s-triazine were tested for their ability to inactivate the human DNA repair protein, $O^6$-alkylguanine-DNA alkyltransferase (AGT, alkyltransferase). Two classes of compounds were identified as being significantly better than $O^6$-benzylguanine (the prototype low-molecular-weight inactivator) in inactivating AGT in human HT29 colon tumor cell extracts. These were 8-substituted $O^6$-benzylguanines bearing electron-withdrawing groups at the 8-position and 5-substituted 2,4-diamino-6-benzyloxypyrimidines bearing electron-withdrawing groups at the 5-position. The latter derivatives were also more effective than $O^6$-benzylguanine in inactivating AGT in intact HT29 colon tumor cells. Both types of compounds were as effective or more effective than $O^6$-benzylguanine in enhancing cell killing by 1,3-bis(2-chloroethyl)-1-nitrosourea (BCNU) of colon, breast and prostate cancer cells grown in culture. Provided 8-substituted $O^6$-benzylguanine derivatives bearing electron-withdrawing substituents at the 8-position and 5-substituted 2,4-diamino-6-benzyloxypyrimidines bearing electron-withdrawing substituents at the 5-position do not exhibit undesirable toxicity, they should be superior to $O^6$-benzylguanine as chemotherapeutic adjuvants for enhancing the effectiveness of antitumor drugs whose mechanism of action involves modification of the $O^6$-position of DNA guanine residues. The specific compounds surveyed for AGT inactivating activity are illustrated below.

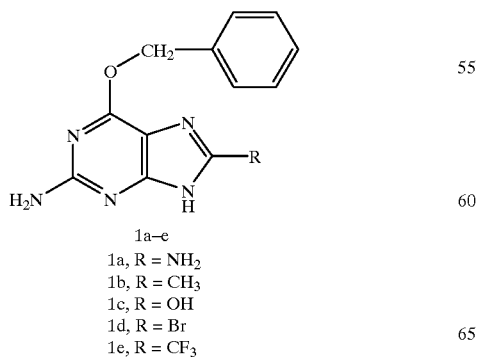

1a–e
1a, R = $NH_2$
1b, R = $CH_3$
1c, R = OH
1d, R = Br
1e, R = $CF_3$

-continued

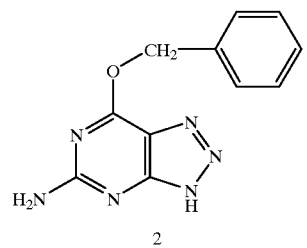

2

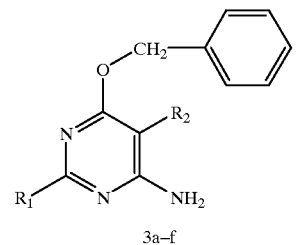

3a–f

3a, $R_1$ = H; $R_2$ = $NO_2$
3b, $R_1$ = $NH_2$; $R_2$ = H
3c, $R_1$ = $NH_2$; $R_2$ = $NH_2$
3d, $R_1$ = $NH_2$; $R_2$ = NO
3e, $R_1$ = $NH_2$; $R_2$ = $NO_2$
3f, $R_1$ = $NH_2$; $R_2$ = Br

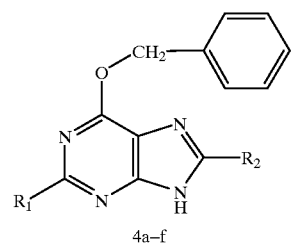

4a–f

4a, $R_1$ = HO; $R_2$ = H
4b, $R_1$ = HO; $R_2$ = OH
4c, $R_1$ = F; $R_2$ = H
4d, $R_1$ = $CH_3CONH$; $R_2$ = OH
4e, $R_1$ = $CH_3NH$; $R_2$ = H
4f, $R_1$ = $(CH_3)_2N$; $R_2$ = H

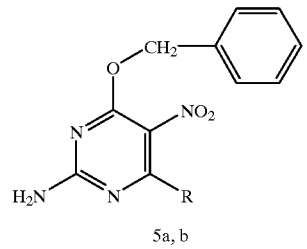

5a, b

5a, R = H
5b, R = $CH_3$

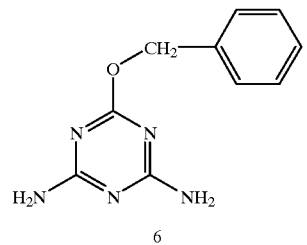

6

-continued

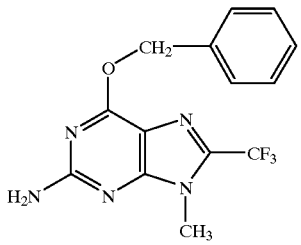

7

Preparations of the 8-substituted O⁶-benzylguanine derivatives 8-amino-O⁶-benzylguanine (1a) and O⁶-benzyl-8-methylguanine (1b) were accomplished by treating 2,8-diamino-6-chloropurine and 2-amino-6-chloro-8-methylpurine, respectively, with sodium benzyloxide in benzyl alcohol. O⁶-Benzyl-8-oxoguanine(O⁶-benzyl-7,8-dihydro-8-oxoguanine, 1c) was prepared by reacting 1,1'-carbonyldiimidazole with 2,4,5-triamino-6-benzyloxypyrimidine (Pfleiderer et al., *Chem. Ber.*, 94, 12–18 (1961)). For convenience the compound is illustrated in the 8-hydroxy tautomeric form although it most probably exists in solution the 8-keto form with a hydrogen attached to the 7-nitrogen atom. O⁶-Benzyl-8-bromoguanine (1d) was prepared by bromination of O⁶-benzylguanine. O⁶-Benzyl-8-trifluoromethylguanine (1e) was prepared by reacting 2-amino-6-chloro-8-trifluoromethylpurine with sodium benzyloxide in benzyl alcohol. 8-Aza-O⁶-benzylguanine (2) was prepared through nitrous acid treatment of 2,4,5-triamino-6-benzyloxypyrimidine. Compound 2 had been prepared previously by another route (Shealy et al., *J. Org. Chem.*, 27, 4518–4523 (1962)).

With respect to the pyrimidine derivatives (3a–f), 4-amino-6-benzyloxy-5-nitropyrimidine (3a) was prepared by treating 4-amino-6-chloro-5-nitropyrimidine (Boon et al., *J. Chem. soc.*, 96–102 (1951)) with sodium benzyloxide in benzyl alcohol. Derivatives 3b–d were prepared by the method of Pfleiderer et al. (*Chem. Ber.*, 94, 12–18 (1961)). 2,4-Diamino-6-benzyloxy-5-nitropyrimidine (3e) and 2,4-diamino-6-benzyloxy-5-bromopyrimidine (3f) were prepared previously by Kosary et al. (*Acta Pharm. Hung.*, 49, 241–247 (1989)).

The purines, O⁶-benzylxanthine (4a) and O⁶-benzyluric acid (4b) were prepared by nitrous acid deamination of O⁶-benzylguanine and O⁶-benzyl-8-oxoguanine, respectively. N²-Acetyl-O⁶-benzyl-8-oxoguanine (N²-acetyl-O⁶-benzyl-7,8-dihydro=8-oxoguanine) (4d) was prepared through acetylation of O⁶-benzyl-8-oxoguanine (1c). O⁶-Benzyl-2-fluorohypoxanthine (4c) was prepared previously by Robins and Robins (*J. Org. Chem.*, 34, 2160–2163 (1969)). This material was treated with methylamine and dimethylamine to produce O⁶-benzyl-N²-methylguanine (4e) and O⁶-benzyl-N²,N²-dimethylguanine (4f), respectively.

Compounds 5a (2-amino-4-benzyloxy-5-nitropyrimidine) and 5b (2-amino-4-benzyloxy-6-methyl-5-nitropyrimidine) were prepared by treating 2-amino-4-chloro-5-nitropyrimidine and 2-amino-4-chloro-6-methyl-5-nitropyrimidine (Boon et al.,*J. Chem. Soc.*, 96–102 (1951)), respectively, with sodium benzyloxide in benzyl alcohol. Compound 6 (2,4-diamino-6-benzyloxy-s-triazine) was prepared previously under similar conditions (Wakabayashi et al., *Nippon Dojo-Hiryyotgaku Zasshi*, 41, 193–200 (1970)). O⁶-Benzyl-8-trifluoromethyl-9-methylguanine (7) was prepared by treating the anion of 1e with methyl iodide in N,N-dimethylformamide.

The ability of these compounds to inactivate the AGT protein in HT29 human colon tumor cell extracts and in intact HT29 cells is summarized in Table 1. The data represent the dose of compound required to produce 50% inactivation in cell-free extracts upon incubation for 30 min or in cells upon incubation for 4 hr.

TABLE 1

AGT-Inactivating Activity of 6-Benzyloxypurine, 6(4)-Benzyloxypyrimidine, and 6-Benzyloxy-s-triazine Derivatives

| | $ED_{50}$ ($\mu M$)[a] | |
|---|---|---|
| Compound | In HT29 cell-free extract | In HT29 cells |
| 2,4-diamino-6-benzyloxy-5-nitrosopyrimidine (3d) | 0.06 | 0.02 |
| 2,4-diamino-6-benzyloxy-5-nitropyrimidine (3e) | 0.06 | 0.02 |
| 8-aza-O⁶-benzylguanine (2) | 0.07 | 0.06 |
| O⁶-benzyl-8-bromoguanine (1d) | 0.08 | 0.06 |
| O⁶-benzylguanine | 0.2 | 0.05 |
| O⁶-benzyl-8-methyl-guanine (1b) | 0.3 | 0.1 |
| O⁶-benzyl-8-oxoguanine (1c) | 0.3 | 0.15 |
| 2,4,5-triamino-6-benzyloxy-pyrimidine (3c) | 0.4 | 0.3 |
| 2-amino-4-benzyloxy-6-methyl-5-nitropyrimidine (5b) | 0.4 | 0.06 |
| 2-amino-4-benzyloxy-5-nitropyrimidine (5a) | 0.4 | 0.05 |
| 8-amino-O⁶-benzyl-guanine (1a) | 0.7 | 2 |
| 2,4-diamino-6-benzyloxy-5-bromopyrimidine (3f) | 2 | 0.8 |
| 2,4-diamino-6-benzyloxy-s-triazine (6) | 4 | 1.0 |
| 2,4-diamino-6-benzyloxy-pyrimidine (3b) | 15 | 5 |
| O⁶-benzyluric acid (4b) | 25 | 45 |
| 4-amino-6-benzyloxy-5-nitropyrimidine (3a) | 28 | 8 |
| O⁶-benzyl-2-fluoro-hypoxanthine (4c) | 48 | 12 |
| O⁶-benzylxanthine (4a) | 60 | 35 |
| N²-acetyl-O⁶-benzyl-8-oxo-guanine (4d) | 65 | 11 |
| O⁶-benzyl-N²-methyl-guanine (4e) | 160 | 60 |
| O⁶-benzyl-N²,N²-dimethyl-guanine (4f) | 200 | 110 |

[a]The effective dose required to produce 50% inactivation in cell-free extracts upon incubation for 30 min or in cells upon incubation for 4 hr. The values for O⁶-benzylguanine are from Moschel et al., J. Med. Chem., 35, 4486–4491 (1992).

Within these series of compounds, O⁶-benzyl-N²-methyl- and O⁶-benzyl-N²,N²-dimethylguanine (4e and 4f) were the least active agents exhibiting $ED_{50}$ values for inactivation of AGT in HT 29 cell extracts of 160 and 200 $\mu M$, respectively. For comparison, the $ED_{50}$ value exhibited by O⁶-benzylguanine was 0.2 $\mu M$ (Table 1). The other 2- and/or 8-substituted 6-benzyloxypurines, N²-acetyl-O⁶-benzyl-8-oxoguanine (4d), O⁶-benzylxanthine (4a), O⁶-benzyl-2-fluorohypoxanthine (4c) and O⁶-benzyluric acid (4b), together with the substituted pyrimidines 4-amino-6-benzyloxy-5-nitropyrimidine (3a) and 2,4-diamino-6-benzyloxypyrimidine (3b), comprised a group of increasingly more active AGT inactivating agents exhibiting intermediate $ED_{50}$ values in the range of 65 to 15 $\mu M$. 2,4-Diamino-6-benzyloxy-s-triazine (6) and 2,4-diamino-6-benzyloxy-5-bromopyrimidine (3f) were considerably more active than 3b indicating that electron-withdrawing groups at the 5-position of a 2,4-diamino-6-benzyloxypyrimidine derivative are positive contributors to efficient AGT inactivation. This is further emphasized by the very high activity exhibited by 2,4-diamino-6-benzyloxy-5-nitroso- (3d) and 2,4-diamino-6-benzyloxy-5-nitropyrimidine (3e), which contain strongly electron-withdrawing nitroso and nitro substituents, respectively. These two derivatives are the most active AGT inactivators tested to date. The observation that 2-amino-4-benzyloxy-5-nitropyrimidine (5a) is much more active than 3a indicates that a 2-amino group is critical for high activity for a 6(4)-benzyloxy-5-nitropyrimidine derivative. An additional alkyl group at the 4(6)-position (e.g., as in 5b) does not enhance activity significantly over that for 5a although an amino group at the 4(6)-position significantly enhances activity. Thus, AGT inactivating activity increases substantially over the series 5a=5b<3d=3e. With these considerations in mind the activity of 2,4,5-triamino-6-benzyloxypyrimidine (3c) seems exceptional and the reasons for its relatively high activity are unclear at present. It is also significant that pyrimidines 5a and 5b are quite active in cells, which is not totally predicted by their corresponding activity in HT 29 cell extracts.

All the $O^6$-benzylguanine analogs 1a–d were much more active than the purines in the series 4a–f and the activity differences among 1a–d also reflect enhancements due to introduction of electron withdrawing groups. Thus, activity increased in the series 8-amino-$O^6$-benzylguanine (1a) <$O^6$-benzyl-8-oxoguanine (1c) <$O^6$-benzyl-8-methylguanine (1b) <$O^6$-benzyl-8-bromoguanine (1d) <8-aza-$O^6$-benzylguanine (2). Indeed, derivatives 1d and 2 were essentially as active as pyrimidines 3d and 3e in cell-free extracts although 1d and 2 were somewhat less active in cells than expected from their activity in cell-free extracts.

The ability of increasing concentrations of 1a–d, 2, and 3c–e to enhance the killing of human HT 29 colon cancer cells, DU-145 prostate cancer cells, and MCF-71 breast cancer cells by BCNU (40 $\mu$M) is shown in Tables 2, 3, and 4, respectively. The data reflect the number of cell colonies that result following exposure to AGT inactivator alone or AGT inactivator 2 hr before exposure to BCNU as described in Dolan et al. (*Proc. Natl. Acad. Sci., U.S.A.*, 87, 5368–5372 (1990)). Data for $O^6$-benzylguanine are included for comparison. As indicated, at 10 $\mu$M concentrations, all the 8-substituted purines with the exception of 1a were as effective as $O^6$-benzylguanine in enhancing the cytotoxicity of BCNU (40 $\mu$M); such treatment killed essentially all the tumor cells. Treatment of the cells with the modified 8-substituted $O^6$-benzylguanine alone or BCNU alone had no significant effect on cell colony number. The comparatively low activity of 1a in all but the breast cancer cells may reflect its poor transport into other tumor cells types or its rapid metabolic conversion to an ineffective AGT inactivator. Its ineffective enhancement of BCNU cytotoxicity parallels its relatively poor AGT inactivating ability in colon tumor cells (Table 1).

For the pyrimidines tested, 2,4,5-triamino-6-benzyloxypyrimidine (3c) was as effective as the 8-substituted $O^6$-benzylguanine derivatives and $O^6$-benzylguanine itself in enhancing BCNU toxicity although the nitroso- and nitropyrimidine derivatives (3d and 3e) were similarly effective at a 4-fold lower dose.

TABLE 2

Killing of HT-29 Colon Cancer Cells by BCNU Combined with AGT Inactivators

| Inactivator | Inactivator Concentration ($\mu$M) | BCNU ($\mu$M) | Colony Formation per 1000 cells |
|---|---|---|---|
| None | | None | 435 ± 63 |
| None | | 40 | 442 ± 34 |
| $O^6$-benzylguanine | 10 | None | 431 ± 33 |
| | 10 | 40 | 13 ± 6 |
| | 2.5 | 40 | 38 ± 15 |
| | 1 | 40 | 277 ± 25 |
| 8-aza-$O^6$-benzylguanine (2) | 10 | None | 537 ± 48 |
| | 10 | 40 | 2 ± 1 |
| | 1 | 40 | 423 ± 42 |

TABLE 2-continued

Killing of HT-29 Colon Cancer Cells by BCNU Combined with AGT Inactivators

| Inactivator | Inactivator Concentration ($\mu$M) | BCNU ($\mu$M) | Colony Formation per 1000 cells |
|---|---|---|---|
| $O^6$-benzyl-8-bromoguanine (1d) | 10 | None | 401 ± 22 |
| | 10 | 40 | 1 ± 0 |
| | 1 | 40 | 299 ± 30 |
| $O^6$-benzyl-8-oxoguanine (1c) | 10 | None | 401 ± 22 |
| | 10 | 40 | <1 |
| | 1 | 40 | 221 ± 15 |
| $O^6$-benzyl-8-methylguanine (1b) | 10 | None | 513 ± 76 |
| | 10 | 40 | <1 |
| | 1 | 40 | 230 ± 51 |
| $O^6$-benzyl-8-aminoguanine (1a) | 10 | None | 504 ± 30 |
| | 10 | 40 | 430 ± 41 |
| | 1 | 40 | 475 ± 26 |
| 2,4,5-triamino-6-benzyloxypyrimidine (3c) | 10 | None | 453 ± 59 |
| | 10 | 40 | 3 ± 1 |
| | 1 | 40 | 487 ± 32 |
| 2,4-diamino-6-benzyloxy-5-nitrosopyrimidine (3d) | 2.5 | None | 528 ± 64 |
| | 2.5 | 40 | <1 |
| | 1 | 40 | 19 ± 4 |
| 2,4-diamino-6-benzyloxy-5-nitropyrimidine (3e) | 2.5 | None | 438 ± 25 |
| | 2.5 | 40 | <1 |
| | 1 | 40 | 45 ± 4 |

TABLE 3

Killing of DU-145 Prostate Cancer Cells by BCNU Combined with AGT Inactivators

| Inactivator | Inactivator Concentration ($\mu$M) | BCNU ($\mu$M) | Colony Formation per 1000 cells |
|---|---|---|---|
| None | | None | 453 ± 81 |
| None | | 40 | 394 ± 76 |
| $O^6$-benzylguanine | 10 | None | 462 ± 68 |
| | 10 | 40 | 28 ± 5 |
| | 1 | 40 | 299 ± 18 |
| 8-aza-$O^6$-benzylguanine | 10 | None | 452 ± 72 |
| | 10 | 40 | 28 ± 5 |
| | 1 | 40 | 248 ± 21 |
| $O^6$-benzyl-8-bromoguanine (1d) | 10 | None | 493 ± 90 |
| | 10 | 40 | 16 ± 3 |
| | 1 | 40 | 267 ± 39 |
| $O^6$-benzyl-8-oxoguanine (1c) | 10 | None | 379 ± 34 |
| | 10 | 40 | 34 ± 3 |
| | 1 | 40 | 329 ± 43 |
| $O^6$-benzyl-8-methylguanine (1b) | 10 | None | 357 ± 43 |
| | 10 | 40 | 50 ± 7 |
| | 1 | 40 | 306 ± 157 |
| $O^6$-benzyl-8-aminoguanine (1a) | 10 | None | 380 ± 36 |
| | 10 | 40 | 435 ± 70 |
| | 1 | 40 | 295 ± 45 |
| 2,4,5-triamino-6-benzyloxypyrimidine (3c) | 10 | None | 429 ± 101 |
| | 10 | 40 | 57 ± 7 |
| | 1 | 40 | 378 ± 60 |
| 2,4-diamino-6-benzyloxy-5-nitrosopyrimidine (3d) | 2.5 | None | 403 ± 35 |
| | 2.5 | 40 | 7 ± 3 |
| | 1 | 40 | 25 ± 4 |
| | 0.25 | 40 | 192 ± 17 |
| 2,4-diamino-6-benzyloxy-5-nitropyrimidine (3e) | 2.5 | None | 407 ± 80 |
| | 2.5 | 40 | 9 ± 2 |
| | 1 | 40 | 59 ± 6 |
| | 0.25 | 40 | 129 ± 26 |

TABLE 4

Killing of MCF-71 Breast Cancer Cells by BCNU Combined with AGT Inactivators

| Inactivator | Inactivator Concentration ($\mu$M) | BCNU ($\mu$M) | Colony Formation per 1000 cells |
|---|---|---|---|
| None | | None | 426 ± 78 |
| None | | 40 | 364 ± 60 |
| $O^6$-benzylguanine | 10 | None | 455 ± 63 |
| | 10 | 40 | 4 ± 2 |
| | 2.5 | 40 | 12 ± 6 |
| 8-aza-$O^6$-benzylguanine (2) | 10 | None | 483 ± 27 |
| | 10 | 40 | 2 ± 1 |
| $O^6$-benzyl-8-bromoguanine (1d) | 10 | None | 380 ± 109 |
| | 10 | 40 | 3 ± 1 |
| | 2.5 | 40 | 4 ± 3 |
| $O^6$-benzyl-8-oxoguanine (1c) | 10 | None | 522 ± 78 |
| | 10 | 40 | 4 ± 2 |
| $O^6$-benzyl-8-methylguanine (1b) | 10 | None | 376 ± 76 |
| | 10 | 40 | 2 ± 1 |
| $O^6$-benzyl-8-aminoguanine (1a) | 10 | None | 432 ± 36 |
| | 10 | 40 | 95 ± 8 |
| 2,4,5-triamino-6-benzyloxypyrimidine (3c) | 10 | None | 448 ± 55 |
| | 10 | 40 | 12 ± 4 |
| 2,4-diamino-6-benzyloxy-5-nitrosopyrimidine (3d) | 2.5 | None | 447 ± 87 |
| | 2.5 | 40 | 2 ± 1 |
| 2,4-diamino-6-benzyloxy-5-nitropyrimidine (3e) | 2.5 | None | 314 ± 49 |
| | 2.5 | 40 | 2 ± 1 |

Although the human alkyltransferase is very sensitive to inactivation by $O^6$-benzylguanine and the various compounds described above, a number of mutants have been generated that are resistant to $O^6$-benzylguanine (Crone and Pegg, Cancer Res., 53, 4750–4753 (1993)). This resistance is probably caused by a reduction in the space surrounding the active site of the alkyltransferase, which limits the access to $O^6$-benzylguanine. These mutants are produced by single base changes in the alkyltransferase DNA-coding sequence causing changes in one or two amino acids in the alkyltransferase (Crone and Pegg, Cancer Res., 53, 4750–4753 (1993)). Thus, as indicated in Table 5, changing the proline residue at position 140 to alanine (protein P140A) or the glycine residue at position 156 to an alanine (protein G156A) causes a 20-fold and a 240-fold increase in resistance to $O^6$-benzylguanine, respectively. The alkyltranferase containing an arginine in place of a proline at residue 138 together with an arginine in place of a proline at residue 140 (Protein P138A/P140A) is 88-fold more resistant to inactivation by $O^6$-benzylguanine. It is possible that such resistant mutants will arise or be selected for in tumors under the selective pressure generated by treatment with $O^6$-benzylguanine plus an alkylating agent. More potent inhibitors and/or those of a smaller size that are better able to fit into the space of the active site of the mutant alkyltransferase can be used to advantage to overcome this resistance.

TABLE 5

Inhibition of Mutant Alkyltransferase Proteins by $O^6$-Benzylguanine or 2,4-Diamino-6-benzyloxy-5-nitrosopyrimidine

| | $ED_{50}$ value ($\mu$M)[a] | |
|---|---|---|
| Protein | $O^6$-benzylguanine | 2,4-diamino-6-benzyloxy-5-nitrosopyrimidine |
| Control | 0.25 | 0.05 |
| P140A | 5 | 0.1 |
| P138A/P140A | 22 | 0.3 |
| G156A | 60 | 1 |

[a]The concentration needed to inactivate 50% of the activity in 30 minutes.

As shown in Table 5, 2,4-diamino-6-benzyloxy-5-nitrosopyrimidine (3d) was 50 to 60 times better at inactivating the mutant alkyltransferases and $O^6$-benzylguanine. Doses of 2,4-diamino-6-benzyloxy-5-nitrosopyrimidine leading to intracellular concentrations greater than 5 $\mu$M will therefore be effective at inactivating such resistant alkyltransferases. Concentrations greater than 200 $\mu$M of $O^6$-benzylguanine would be needed to get such inactivation, and these are much more than can be achieved with this compound in current formulations. However, 8-substituted $O^6$-benzylguanine derivatives that are significantly more potent than $O^6$-benzylguanine may be useful in inactivating mutant alkyltransferases provided their required intracellular concentrations can be achieved. These data for mutant akyltransferase inactivation and the data presented earlier indicate that pyrimidine derivatives bearing electron-withdrawing groups at the 5-position as well as substituted $O^6$-benzylguanine derivatives bearing electron-withdrawing groups at the 8-position are superior to $O^6$-benzylguanine for use as adjuvants in chemotherapy with agents whose mechanism of action, like that of BCNU, involves modification of the $O^6$-position of DNA guanine residues.

Other 8-substituted $O^6$-benzylguanine derivatives bearing electron-withdrawing 8-substituents (e.g., $NO_2$) are readily available. For example, $O^6$-benzyl-8-nitroguanine could be prepared by treatment of 8-nitroguanine (Jones and Robins, J. Am. Chem. Soc., 82, 3773–3779 (1960)) with phosphorus oxychloride to produce 2-amino-6-chloro-8-nitropurine which when treated with sodium benzyloxide in benzyl alcohol would produce the desired $O^6$-benzyl-8-nitroguanine.

Additional 2,4-diamino-6-benzyloxyprimidine derivatives bearing electron-withdrawing groups other than halogen or nitro groups (e.g., formyl or cyano groups) could also be readily prepared. 2,4-Diamino-5-formyl-6-hydroxypyrimidine, a known compound (Delia and Otteman, Heterocycles, 20, 1805–1809 (1983)), can be treated with phosphorus oxychloride to produce a 2,4-diamino-6-chloro-5-formylpyrimidine intermediate, which on treatment with sodium benzyloxide in benzyl alcohol produces 2,4-diamino-6-benzyloxy-5-formylpyrimidine. Treatment of the formyl pyrimidine with hydroxylamine affords 2,4-diamino-6-benzyloxy-5-cyanopyrimidine. The preparation of a large number of 5-substituted 6(4)-benzyloxypyrimidines or 8-substituted $O^6$-benzylguanine derivatives is possible for those skilled in the art of synthesis of heterocyclic aromatic compounds (D. J. Brown, "The Pyrimidines," in The Chemistry of Heterocyclic Compounds, Vol. 16, A. Weissberger, Ed., Wiley Interscience, New York, 1962; D. J. Brown, "The Pyrimidines," Supplement I, in The Chemistry of Heterocyclic Compounds, Vol. 16, A. Weissberger and E. C. Taylor, Eds., Wiley Interscience, New York, 1970; J. H. Lister, "Fused Pyrimidines Part II Purines," in *The Chemistry of Heterocyclic Compounds,* Vol. 24 Part II, A. Weissberger and E. C. Taylor, Eds., Wiley Interscience, New York, 1971).

Because many 9-substituted $O^6$-benzylguanine derivatives exhibit excellent AGT inactivation properties (Moschel et al., *J. Med. Chem.,* 35, 4486–4491 (1992); Chae et al., *J. Med. Chem.,* 37, 342–347 (1994)), 8,9-disubstituted analogs are expected to be similarly active. These can be readily prepared by reacting the anion of 8-substituted $O^6$-benzylguanines (e.g., 1a–e) or the anion of 8-aza-$O^6$-benzylguanine (2) with any of the range of compounds already described (Moschel et al., *J. Med. Chem.,* 35, 4486–4491 (1992); Chae et al., *J. Med. Chem.,* 37, 342–347 (1994)) to produce a mixture of isomeric 7,8- and 8,9-disubstituted $O^6$-benzylguanine derivatives. The desired 8,9-disubstituted derivative can be isolated and purified by silica gel column chromatography as already described (Moschel et al., *J. Med. Chem.,* 35, 4486–4491 (1992); Chae et al., *J. Med. Chem.,* 37, 342–347 (1994)). Compound 7 was prepared by treating the anion of compound 1e with methyl iodide in N,N-dimethylformamide.

The $O^6$-substituted compound of the present invention can be administered in any suitable manner to a mammal for the purpose of enhancing the chemotherapeutic treatment of a particular cancer. Although more than one route can be used to administer a particular compound, a particular route can provide a more immediate and more effective reaction than another route. Accordingly, the described methods provided herein are merely exemplary and are in no way limiting.

Generally, the $O^6$-substituted compounds of the present invention as described above will be administered in a pharmaceutical composition to an individual afflicted with a cancer. Those undergoing or about to undergo chemotherapy can be treated with the $O^6$-substituted compounds separately or in conjunction with other treatments, as appropriate. In therapeutic applications, compositions are administered to a patient in an amount sufficient to elicit an effective depression of AGT activity thereby potentiating the cytotoxicity of the aforedescribed chemotherapeutic treatment. An amount adequate to accomplish this is defined as a "therapeutically effective dose," which is also an "AGT inactivating effective amount." Amounts effective for a therapeutic or prophylactic use will depend on, e.g., the stage and severity of the disease being treated, the age, weight, and general state of health of the patient, and the judgment of the prescribing physician. The size of the dose will also be determined by the $O^6$-substituted compound selected, method of administration, timing and frequency of administration as well as the existence, nature, and extent of any adverse side-effects that might accompany the administration of a particular $O^6$-substituted compound and the desired physiological effect. It will be appreciated by one of skill in the art that various disease states may require prolonged treatment involving multiple administrations, perhaps using a series of different AGT inactivators and/or chemotherapeutic agents in each or various rounds of administration.

Suitable chemotherapeutic agents usefully administered in coordination with the $O^6$-substituted compounds of the present invention include alkylating agents, such as chloroethylating and methylating agents. Such agents may be administered using conventional techniques such as those described in Wasserman et al., *Cancer,* 36, pp. 1258–1268 (1975), and *Physician' Desk Reference,* 48th ed., Edward R. Barnhart publisher (1994). For example, 1,3-bis(2-chloroethyl)-1-nitrosourea (carmustine or BCNU, Bristol-Myers, Evansville, Ind.) may be administered intravenously at a dosage of from about 150 to 200 mg/m$^2$ every six weeks. Another alkylating agent, 1-(2-chloroethyl)-3-cyclohexyl-1-nitrosourea (lomustine or CCNU, Bristol-Myers), may be administered orally at a dosage of about 130 mg/m$^2$ every six weeks. Other alkylating agents may be administered in appropriate dosages via appropriate routes of administration known to skilled medical practitioners.

Suitable doses and dosage regimens can be determined by conventional range-finding techniques known to those of ordinary skill in the art. Generally, treatment is initiated with smaller dosages that are less than the optimum dose of the compound. Thereafter, the dosage is increased by small increments until the optimum effect under the circumstances is reached. The present inventive method typically will involve the administration of about 0.1 μg to about 50 mg of one or more of the compounds described above per kg body weight of the individual. For a 70 kg patient, dosages of from about 10 μg to about 200 mg of $O^6$-substituted compound would be more commonly used, possible followed by further lesser dosages from about 1 μg to about 1 mg of $O^6$-substituted compound over weeks to months, depending on a patient's physiological response, as determined by measuring cancer-specific antigens or other measurable parameters related to the tumor load of a patient.

It must be kept in mind that the compounds and compositions of the present invention generally are employed in serious disease states, that is, life-threatening or potentially life-threatening situations. In such cases, in view of the minimization of extraneous substances and the relative nontoxic nature of the $O^6$-substituted compounds, it is possible and may be felt desirable by the treating physician to administer substantial excesses of these $O^6$-substituted compounds.

Single or multiple administrations of the compounds can be carried out with dose levels and pattern being selected by the treating physician. In any event, the pharmaceutical formulations should provide a quantity of AGT-inactivating compounds of the invention sufficient to effectively enhance the cytotoxic impact of the chemotherapy.

The pharmaceutical compositions for therapeutic treatment are intended for parenteral, topical, oral or local administration and generally comprise a pharmaceutically acceptable carrier and an amount of the active ingredient sufficient to reduce, and preferably prevent, the activity of the AGT protein. The carrier may be any of those conventionally used and is limited only by chemico-physical considerations, such as solubility and lack of reactivity with the compound, and by the route of administration.

Examples of pharmaceutically acceptable acid addition salts for use in the present inventive pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic acids, and arylsulphonic, for example.

The pharmaceutically acceptable excipients described herein, for example, vehicles, adjuvants, carriers or diluents, are well-known to those who are skilled in the art and are readily available to the public. It is preferred that the pharmaceutically acceptable carrier be one that is chemically inert to the active compounds and one that has no detrimental side effects or toxicity under the conditions of use. Such pharmaceutically acceptable excipients preferably include saline (e.g., 0.9% saline), Cremophor EL (which is a derivative of castor oil and ethylene oxide available from Sigma Chemical Co., St. Louis, Mo.) (e.g., 5% Cremophor EL/5% ethanol/90% saline, 10% Cremophor EL/90% saline, or 50% Cremophor EL/50% ethanol), propylene glycol (e.g., 40% propylene glycol/10% ethanol/50% water), polyethylene glycol (e.g., 40% PEG 400/60% saline), and alcohol (e.g., 40% t-butanol/60% water). The most preferred pharmaceutical excipient for use in conjunction with the present invention is polyethylene glycol, such as PEG 400, and particularly a composition comprising 40% PEG 400 and 60% water or saline.

The choice of excipient will be determined in part by the particular $O^6$-substituted compound chosen, as well as by the particular method used to administer the composition. Accordingly, there is a wide variety of suitable formulations of the pharmaceutical composition of the present invention.

The following formulations for oral, aerosol, parenteral, subcutaneous, intravenous, intramuscular, interperitoneal, rectal, and vaginal administration are merely exemplary and are in no way limiting.

The pharmaceutical compositions can be administered parenterally, e.g., intravenously, subcutaneously, intradermally, or intramuscularly. Thus, the invention provides compositions for parenteral administration that comprise a solution of the $O^6$-substituted compound dissolved or suspended in an acceptable carrier suitable for parenteral administration, including aqueous and non-aqueous, isotonic sterile injection solutions.

Overall, the requirements for effective pharmaceutical carriers for parenteral compositions are well known to those of ordinary skill in the art. See *Pharmaceutics and Pharmacy Practice*, J. B. Lippincott Company, Philadelphia, Pa., Banker and Chalmers, eds., pages 238–250 (1982), and *ASHP Handbook on Injectable Drugs,* Toissel, 4th ed., pages 622–630 (1986). Such solutions can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound may be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, or synthetic oils. Specific examples of oils useful in such formulations include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations typically will contain from about 0.5 to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Topical formulations, including those that are useful for transdermal drug release, are well-known to those of skill in the art and are suitable in the context of the present invention for application to skin.

Formulations suitable for oral administration require extra considerations considering the peptidyl and/or carbohydrate nature of some of the $O^6$-substituted compounds of the present invention and the likely breakdown thereof if such compounds are administered orally without protecting them from the digestive secretions of the gastrointestinal tract. Such a formulation can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavour, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The O$^6$-substituted compounds of the present invention, alone or in combination with other suitable components, can be made into aerosol formulations to be administered via inhalation. The compounds are preferably supplied in finely divided form along with a surfactant and propellant. Typical percentages of active compound are 0.01%–20% by weight, preferably 1%–10%. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%–20% by weight of the composition, preferably 0.25%–5%. The balance of the composition is ordinarily propellant. A carrier can also be included as desired, e.g., lecithin for intranasal delivery. These aerosol formulations can be placed into acceptable pressurized propellants, such as dichlorodifluoromethane, propane, nitrogen, and the like. They also may be formulated as pharmaceuticals for non-pressured preparations, such as in a nebulizer or an atomizer. Such spray formulations may be used to spray mucosa.

Additionally, the compounds and polymers useful in the present invention methods may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

The concentration of the $O^6$-substituted compounds of the present invention in the pharmaceutical formulations can vary widely, i.e., from less than about 1%, usually at or at least about 10%, to as much as 20 to 50% or more by weight, and will be selected primarily by fluid volumes, viscosities, etc., in accordance with the particular mode of administration selected.

Thus, a typical pharmaceutical composition for intravenous infusion could be made up to contain 250 ml of sterile Ringer's solution, and 100 mg of the $O^6$-substituted compound. Actual methods for preparing parenterally administrable compounds will be known or apparent to those skilled in the art and are described in more detail in, for example, *Remington's Pharmaceutical Science* (17th ed., Mack Publishing Company, Easton, Pa., 1985).

It will be appreciated by one of ordinary skill in the art that, in addition to the aforedescribed pharmaceutical compositions, the $O^6$-substituted compounds of the present inventive method may be formulated as inclusion complexes, such as cyclodextrin inclusion complexes, or liposomes. Liposomes serve to target the compounds to a particular tissue, such as lymphoid tissue or cancerous hepatic cells. Liposomes can also be used to increase the half-life of the $O^6$-substituted compound. Liposomes useful in the present invention include emulsions, foams, micelles, insoluble monolayers, liquid crystals, phospholipid dispersions, lamellar layers and the like. In these preparations, the $O^6$-substituted compound to be delivered is incorporated as part of a liposome, alone or in conjunction with a suitable chemotherapeutic agent. Thus, liposomes filled with a desired $O^6$-substituted compound of the invention can be directed to the site of a specific tissue type, hepatic cells, for example, where the liposomes then deliver the selected chemotherapeutic-enhancement compositions. Liposomes for use in the invention are formed from standard vesicle-forming lipids, which generally include neutral and negatively charged phospholipids and a sterol, such as cholesterol. The selection of lipids is generally guided by consideration of, for example, liposome size and stability of the liposomes in the blood stream. A variety of methods are available for preparing liposomes, as described in, for example, Szoka et al., *Ann. Rev. Biophys. Bioeng.,* 9, 467 (1980), and U.S. Pat. Nos. 4,235,871, 4,501,728, 4,837,028, and 5,019,369. For targeting to the cells of a particular tissue type, a ligand to be incorporated into the liposome can include, for example, antibodies or fragments thereof specific for cell surface determinants of the targeted tissue type. A liposome suspension containing an $O^6$-substituted compound may be administered intravenously, locally, topically, etc. in a dose that varies according to the mode of administration, the $O^6$-substituted compound being delivered, the stage of disease being treated, etc.

While the efficacy of the $O^6$-substituted compounds of the present invention has been demonstrated with respect to particular types of cancerous cells, e.g., colon, prostate, and breast cancer cells, the present invention has applicability to the treatment of any type of cancer capable of being treated with an antineoplastic alkylating agent which causes cytotoxic lesions at the $O^6$-position of guanine. Such cancers include, for example, colon tumors, prostate tumors, brain tumors, lymphomas, leukemias, breast tumors, ovarian tumors, lung tumors, Wilms' tumor, rhabdomyosarcoma, multiplemyeloma, stomach tumors, soft-tissue sarcomas, Hodgkin's disease, and non-Hodgkin's lymphomas.

Similarly, in view of the mode of action of the $O^6$-substituted compounds of the present invention, such compounds can be used in conjunction with any type of antineoplastic alkylating agent which causes cytotoxic lesions at the $O^6$-position of guanine. Such antineoplastic alkylating agents include, for example, chloroethylating agents (e.g. chloroethylnitrosoureas and chloroethyltriazines) and monofunctional alkylating agents such as Streptozotocin, Procarbazine, Dacarbazine, and Temozolomide.

Among the chloroethylating agents, the most frequently used chemotherapeutic drugs are 1-(2-chloroethyl)-3-cyclohexyl-1-nitrosourea (CCNU, limustine), 1,3-bis(2-chloroethyl)-1-nitrosourea (BCNU, carmustine), 1-(2-chloroethyl)-3-(4-metylcyclohexyl)-1-nitrosourea (MeCCNU, semustine), and 1-(2-chloroethyl)-3-(4-amino-2-methyl-5-pyrimidinyl)methyl-1-nitrosourea (ACNU). These agents have been used clinically against tumors of the central nervous system, multiple myeloma, melanoma, lymphoma, gastrointestinal tumors, and other solid tumors (Colvin and Chabner, Alkylating Agents. In: Cancer Chemotherapy: Principles and Practice, Chabner and Collins, eds., Lippincott, Philadelphia, pp. 276–313 (1990); McCormick and McElhinney, *Eur. J. Cancer,* 26, 207–221 (1990)). Chloroethylating agents currently under development with fewer side effects are 1-(2-chloroethyl)-3-(2-hydroxyethyl)-1-nitrosourea (HECNU), 2-chloroethylmethylsulfonylmethanesulfonate (Clomesone), and 1-[N-(2-chloroethyl)-N-nitrosoureido] ethylphosphonic acid diethyl ester (Fotemustine) (Colvin and Chabner, Alkylating Agents. In: Cancer Chemotherapy: Principles and Practice, Chabner and Collins, eds., Lippincott, Philadelphia, pp. 276–313 (1990); McCormick and McElhinney, *Eur. J. Cancer,* 26, 207–221 (1990). Methylating chemotherapeutic agents include Streptozotocin (2-deoxy-2-(3-methyl-3-nitrosoureido)-D-glucopyranose), Procarbazine (N-(1-methylethyl)-4-[(2-methylhydrazino)methyl]benzamide), Dacarbazine or DTIC (5-(3,3-dimethyl-1-triazenyl)-1H-imidazole-4-carboxamide), and Temozolomide (8-carbamoyl-3-methylimidazo[5,1-d]-1,2,3,5-tetrazine-4-(3H)-one). Temozolomide is active against malignant melanomas, brain tumors, and mycosis fungoides. Streptozotocin is effective against pancreatic tumors. Procarbazine is used to treat Hodgkin's disease and brain tumors, and DTIC is used in treatment of melanoma and lymphomas (Colvin and Cabner, Alkylating Agents. In: Cancer Chemotherapy: Principles and Practice, Chabner and Collins, eds., Lippincott, Philadelphia, pp. 276–313 (1990); Longo, *Semin. Concol.*, 17, 716–735 (1990)).

The examples set forth below describe the syntheses of the aforementioned compounds. As regards the methods and materials set forth in these examples, $^1$H-NMR spectra were recorded on a Varian VXR 500S spectrometer equipped with Sun 2/110 data stations or a Varian XL 200 instrument interfaced to an Advanced data system. Samples were dissolved in DMSO-$d_6$ with Me$_4$Si as an internal standard. EI mass spectra were obtained on a reversed geometry VG Micromass ZAB-2F spectrometer interfaced to a VG 2035 data system. Elemental analyses were performed by Galbraith Laboratories, Inc., Knoxville, Tenn.

Most of the reagents and solvents were from Aldrich Chemical Co., Inc., Milwaukee, Wis. 8-Aza-O$^6$-benzylguanine (2) (Shealy et al., *J. Org. Chem.*, 27, 4518–4523 (1962)), 2,4-diamino-6-benzyloxypyrimidine (3b) (Pfleiderer and Lohrmann, *Chem. Ber.*, 94, 12–18 (1961)), 2,4,5-triamino-6-benzyloxypyrimidine (3c) (Pfleiderer and Lohrmann, *Chem. Ber.*, 94, 12–18 (1961)), 2,4-diamino-6-benzyloxy-5-nitrosopyrimidine (3d) (Pfleiderer and Lohrman, *Chem. Ber.*, 94, 12–18 (1961)), 2,4-diamino-6-benzyloxy-5-nitropyrimidine (3e) (Kosary et al., *Acta. Pharm. Hung.*, 49, 241–247 (1989)), 2,4-diamino-6-benzyloxy-5-bromopyrimidine (3f) (Kosary et al., *Acta Pharm. Hung.*, 49, 241–247 (1989)), 4-amino-6-benzyloxy-5-nitropyrimidine (3a) and O$^6$-benzyl-2-fluorohypoxanthine (4c) (Robins and Robins, *J. Org. Chem.*, 34, 2160–2163 (1969)) were prepared previously. Alternative synthetic methods are provided below for some of these compounds together with spectroscopic data not provided previously. AGT inactivation studies were carried out as described in Moschel et al., *J. Med. Chem.* 35, 4486–4491 (1992). Cell killing experiments involving various AGT inactivators in combination with BCNU were carried out as in Dolan, et al. (*Proc. Natl. Acad. Sci. U.S.A.*, 87, 5368–5372 (1990)). Cells were treated for 2 h with AGT inactivator prior to exposure to BCNU.

EXAMPLE 1

2,8-Diamino-6-chloropurine

A suspension of 8-aminoguanine (Fischer, *Z. Physiol. Chem.*, 60, 69 (1909); Beaman et al., in Zorback and Tipson, *Synthetic Procedures in Nucleic Acid Chemistry*, Vol. 1, pp 41–43, John Wiley & Sons, New York, 1968) (3.0 g, 18.1 mmol) in phosphorus oxychloride (90 mL) and N,N-diethylaniline (3 mL) was refluxed for 30 min and the excess phosphorus oxychloride was evaporated under reduced pressure. Ice (20 g) was added slowly to the resulting solution and the pH was adjusted to 6 with a concentrated aqueous sodium hydroxide solution. A yellow solid formed and was collected by filtration, washed with water, and dried to give a green solid. Crystallization from water with charcoal treatment produced 2,8-diamino-6-chloropurine as a white solid: yield, 2.11 g (63%); mp>275° C. dec.; $^1$H NMR δ 6.09 (s, 2 H, NH$_2$, exchange with D$_2$O), 6.71 (s, 2 H, NH$_2$, exchange with D$_2$O); MS (EI) calcd. m/z for $C_5H_5N_6^{35}Cl$ 184.0264, found 184.0266; calcd. m/z $C_5H_5N_6^{37}Cl$ 186.0235, found 186.0237.

EXAMPLE 2

8-Amino-O$^6$-benzylguanine (1a)

2,8-Diamino-6-chloropurine (0.9 g, 4.9 mmol) was added to the solution of sodium (0.22 g, 10 mmol) in benzyl alcohol (9.0 mL). The solution was heated in a 130° C. oil bath for 5 h, and was poured into water (100 mL) with constant stirring for 10 min. Undissolved solid was removed by filtration and the filtrate was neutralized with glacial acetic acid. The solution was mixed with methanol (100 mL), and half of the aqueous methanol solution was loaded on a 3×80 cm Sephadex LH-20 column eluted with methanol/water (1:1) at 1 mL/min. Column eluent was continously monitored at 280 nm and fractions (10 mL) were collected. The remainder of the reaction mixture in MeOH/H$_2$O was chromatographed separately under identical conditions. The desired product eluted in fractions 100–130. Evaporation of solvent from the pooled fractions 100–130 from both chromatographic runs afforded analytically pure 1a: yield, 0.26 g (21%); mp 269–271° C. dec.; UV (pH 1) $\lambda_{max}$ 241 nm (ε=0.699×10$^4$), 300 (1.109×10$^4$); (pH 6.9) 250 (sh) (0.447×10$^4$), 292 (1.027×10$^4$); (pH 13) 255 (sh) (0.355×10$^4$), 295 (0.932×10$^4$); $^1$H NMR δ 5.41 (s, 2 H, ArCH$_2$), 5.70 (s, 2 H, NH$_2$, exchange with D$_2$O), 6.18 (s, 2 H, NH$_2$, exchange with D$_2$O), 7.25–7.55 (m, 5 H, ArH), 11.1 (br, s, 1 H, NH, exchanges with D$_2$O); MS (EI) calcd. m/z for $C_{12}H_{12}N_6O$ 256.1072, found 256.1059; Anal. ($C_{12}H_{12}N_6O$) C, H, N.

EXAMPLE 3

2-Amino-6-chloro-8-methylpurine

A suspension of 8-methylguanine (Daves et al., J. Am. Chem. Soc., 82, 2633–2640 (1960)) (1.0 g, 6.1 mmol) in phosphorous xoychloride (30 mL) and N,N-diethylaniline (1 mL) was refluxed for 3 h. The excess phosphorous oxychloride was evaporated under reduced pressure. The resulting brown oil was dissolved in ice-water and was neutralized with a concentrated aqueous NaOH solution. After evaporation of the solvent, the solid residue was suspended in 70 mL of H$_2$O. Undissolved solid was filtered off, and the filtrate was loaded on a 3×80 cm Sephadex LH-20 column eluted with methanol/water (1:1) at 1 mL/min. Column eluent was continuously monitored at 280 nm and fractions (10 mL) were collected. Evaporation of pooled fractions 50–60 produced 2-amino-6-chloro-8-methylpurine as a crude solid. Crystallization from ethanol/water with charcoal treatment afforded 2-amino-6-chloro-8-methylpurine as as a white solid: yield, 0.57 g (51%); mp >265° C. dec.; $^1$H NMR δ2.39 (s, 3 H, CH$_3$), 6.62 (s, 2 H, NH$_2$, exchange with D$_2$O), 12.56 (s, 1 H, NH, exchanges with D$_2$O); MS (EI) calcd. m/z for $C_6H_6N_5^{35}Cl$ 183.0312, found 183.0309; calcd. m/z for $C_6H_6N_5^{37}Cl$ 185.0283, found 185.0286.

EXAMPLE 4

O$^6$-Benzyl-8-methylguanine (1b)

Sodium (0.1 g, 4.4 mmol) was stirred in 4.1 mL of benzyl alcohol until all sodium had reacted. 2-Amino-6-chloro-8-methylpurine (0.41 g, 2.2 mmol) was added, and the reaction mixture was heated in a 130° C. oil bath for 5 h. After cooling to room temperature 40 mL of ether was added to remove excess benzyl alcohol. The sticky precipitate that formed was collected by filtration and was dissolved in water (50 mL). The pH of the yellow solution was adjusted to 5–6 with glacial acetic acid. The solution was mixed with methanol (50 mL) and was loaded on a 3×80 cm Sephadex LH-20 column eluted with methanol/water (1:1) at 1 mL/min. Column eluent was continuously monitored at 280 nm and fractions (10 mL) were collected. Evaporation of pooled fractions 78–93 afforded analytically pure 1b: yield, 0.25 g (44%); mp 214–216° C.; UV (pH 1 )$\lambda_{max}$ 238 nm (sh) ($\epsilon$=0.648×10$^4$), 290 (1.136×10$^4$); (pH 6.9) 242 (0.758×10$^4$), 284 (0.897 ×10$^4$); (pH 13) 240 (sh) (0.495×10$^4$), 286 (0.932×10$^4$); $^1$H NMR δ2.33 (s, 3 H, CH$_3$), 5.46 (s, 2 H, ArCH$_2$), 6.17 (s, 2 H, NH$_2$, exchange with D$_2$O), 7.34–7.51 (m, 5 H, ArH), 12.18 (br s, 1 H, NH, exchanges with D$_2$O),.; MS (EI) calcd. m/z for C$_{13}$H$_{13}$N$_5$O 255.1120, found 255.1125; Anal. (C$_{13}$H$_{13}$N$_5$O.¼ H$_2$O) C, H, N.

EXAMPLE 5

O$^6$-Benzyl-8-oxoguanine (1c)

2,4,5-Triamino-6-benzyloxypyrimidine (Pfleiderer et al., Chem. Ber., 94, 12–18 (1961)) (1.85 g, 8 mmol) and 1,1'-carbonyldiimidazole (1.30 g, 8 mmol) were dissolved in anhydrous N,N-dimethylformamide (5 mL) under argon. The solution was stirred at room temperature overnight and was mixed with water (200 mL) to precipitate a white solid. The solid was collected by filtration, and dissolved in 250mL of aqueous 2 N NaOH solution. Undissolved material was removed by filtration, and the filtrate was neutralized with glacial acetic acid to precipitate a white solid. The solid was collected by filtration, was washed with water, and was recrystallized from 50% aqueous ethanol to afford analytically pure 1c: yield, 1.63 g (79%); mp 256–257 ° C. dec.; UV (pH 1) $\lambda_{max}$ 243 nm ($\epsilon$=0.717×10$^4$), 306 (1.499× 10$^4$); (pH 6.9) 243 (0.915×10$^4$), 290 (1.108×10$^4$); (pH 13) 249 (sh) (0.443×10$^4$), 293 (1.368×10$^4$); $^1$H NMR δ5.41 (s, 2 H, ArCH$_2$), 6.13 (s, 2 H, NH$_2$, exchange with D$_2$O), 7.33–7.51 (m, 5 H, ArH), 10.46 (s, 1 H, exchanges with D$_2$O), 11.04 (s, 1 H, exchanges with D$_2$O); MS (EI) Calcd. m/z for C$_{12}$H$_{11}$N$_5$O$_2$: 257.0912. Found: 257.0914. Anal. (C$_{12}$H$_{11}$N$_5$O$_2$. ½ H$_2$O) C, N, H.

EXAMPLE 6

O$^6$-Benzyl-8-bromoguanine (1d)

Bromine (0.26 mL, 5.1 mmol) was added slowly to the solution of O$^6$-benzylguanine (1.205 g, 5.0 mmol) in anhydrous DMF (10 mL) under argon. The resulting deep green solution was stirred at room temperature overnight. The solution was mixed with water (70 mL) to precipitate crude product. This product was collected by filtration and was dissolved in 50% aqueous methanol (100 mL). The solution was loaded on a 3×80 cm Sephadex LH-20 column eluted with methanol/water (1:1) at 1 mL/min. Column eluent was continuously monitored at 280 nm and fractions (10 mL) were collected. The desired product eluted in fractions 110–190. Evaporation of solvent from the pooled fractions 110–190 afforded 1d as a pale yellow solid. Crystallization from ethanol/water (1:1) produced analytically pure 1d: yield, 0.166 g (10%); mp 135–137° C. dec.; UV (pH 1)$\lambda_{max}$ 236 nm (sh) ($\epsilon$=0.517×10$^4$), 294 (1.429×10$^4$); (pH 6.9) 244 (0.666×10$^4$), 287 (1.043×10$^4$); (pH 13) 245 (sh) (0.544× 10$^4$), 289 (1.030×10$^4$); $^1$H NMR δ5.45 (s, 2 H, ArCH$_2$), 6.35 (s, 2 H, NH$_2$, exchange with D$_2$O), 7.34–7.52 (m, 5 H, ArH), 13.08 (b s, 1 H, NH, exchanges with D$_2$O); MS (EI) calcd. m/z for C$_{12}$H$_{10}$N$_5$O$^{79}$Br 319.0068, found 319.0069; calcd. m/z for C$_{12}$H$_{10}$ N$_5$O$^{81}$Br 321.0048, found 321.0048; Anal. (C$_{12}$H$_{10}$N$_5$OBr3/2 H$_2$O) C, H, N, Br.

EXAMPLE 7

8-Aza-O$^6$-Benzylguanine (2)

Glacial acetic acid (1 mL) was added into the mixture of 2,4,5-triamino-6-benzyloxypyrimidine (0.231 g, 1.0 mmol) and sodium nitrite (0.069 g, 1.0 mmol) in acetone (5 mL). The resulting mixture was stirred at room temperature for 2 h. The solution was poured in water (100 mL) with stirring to precipitate a crude solid. The solid was collected by filtration and air dried. Crystallization from ethanol/water (1:1) with charcoal treatment produced 2 as a white solid: yield, 105 mg (43%); mp 191–192° C. (192–193° C. ; Shealy et. al., J. Org. Chem., 27, 4518–4523 ((1962)); $^1$H NMR δ5.56 (s, 2 H, ArCH$_2$), 7.00 (s, 2 H, NH$_2$, exchange with D$_2$O), 7.41–7.58 (m, 5 H, ArH); MS (EI) calcd. m/z for C$_{11}$H$_{10}$N$_6$O 242.0916, found 242.0924.

EXAMPLE 8

4-Amino-6-benzyloxy-5-nitropyrimidine (3a)

4-Amino-6-chloro-5-nitropyrimidine (Boon et al., J. Chem. Soc., 96–102 (1951)) (1.5 g, 8.6 mmol) was added to a solution of sodium (0.23 g, 9.9 mmol) in benzyl alcohol (14 mL). The solution was heated in a 130° C. oil bath for 3.5 h, and was poured into benzene (50 mL). A yellow solid was collected by filtration and washed with benzene. Crystallization from benzene/ether afforded an analytically pure sample of 3a: yield, 0.71 g (34%); mp 149–150° C.; UV (pH 1) $\lambda_{max}$ 284 nm ($\epsilon$=0.368×10$^4$), 333 (0.488×10$^4$); (pH 6.9) 284 (0.329×10$^4$), 336 (0.470×10$^4$); (pH 13) 290 (0.344× 10$^4$), 333 (0.494×10$^4$); $^1$H NMR δ5.50 (s, 2 H, ArCH$_2$), 7.33–7.49 (m, 5 H, ArH), 8.12–8.24 (br d, 2 H, NH$_a$ and NH$_b$, exchange with D$_2$O), 8.24 (s, 1 H, H-2); MS (EI) calcd. m/z for C$_{11}$H$_{10}$N$_4$O$_3$ 246.0752, found 246.0751; Anal. (C$_{11}$H$_{10}$N$_4$O$_3$) C, H, N.

EXAMPLE 9

2,4-Diamino-6-benzyloxy-5-nitropyrimidine (3e)

2,4-Diamino-6-chloro-5-nitropyrimidine (O'Brien et. al., J. Med. Chem., 9, 573–575 (1966)) (1.0 g, 5.28 mmol) was added to a solution of sodium (0.14 g, 6.08 mmol) in benzyl alcohol (9 mL). The solution was heated in a 160 ° C. oil bath for 3.5 h and the solvent was evaporated under reduced pressure to provide a yellow solid. This solid was washed with water, and air dried. Crystallization from benzene/ether gave a pale yellow filamentous solid: yield, 0.69 g (50%); mp 194–195° C. (171° C.; Kosary et. al., Acta. Pharm. Hung., 49, 241–247 (1989)); UV (pH 1) $\lambda_{max}$ 236 nm (sh) ($\epsilon$=1.452×10$^4$), 264 (0.522×10$^4$), 321 (1.294×10$^4$); (pH 6.9) 242 (sh) (0.965×10$^4$), 337 (1.493×10$^4$); (pH 13) 242 (sh) (0.952×10$^4$), 338 (1.479×10$^4$); $^1$H NMR δ5.43 (s, 2 H, ArCH$_2$), 7.26 (br s, 2 H, NH$_2$, exchange with D$_2$O), 7.33–7.51 (m, 5 H, ArH), 7.93 (br s, 2 H, NH$_2$, exchange with D$_2$O); MS (EI) calcd. m/z for C$_{11}$H$_{11}$N$_5$O$_3$ 261.0861, found 261.0866; Anal. (C$_{11}$H$_{11}$N$_5$O$_3$).

EXAMPLE 10

O$^6$-Benzylxanthine (4a)

A suspension of O$^6$-benzylguanine (0.83 g, 3.4 mmol) in acetone (15mL) was poured into a solution of sodium nitrite (5 g) in 15 mL of H$_2$O. Acetic acid (8 mL) was added to the suspension with stirring. Minimum amounts of acetone were added as necessary to dissolve any suspended solid. The resulting pale yellow-green solution was stirred for 3 h. A pale green precipitate that formed was collected by filtration and washed with water (200 mL). Recrystallization of the air-dried solid from ethanol/water (1:1) afforded analytically pure 4a: yield, 0.43 g (52%); mp 145–147° C. dec.; UV (pH 1) $\lambda_{max}$ 270 nm ($\epsilon$=0.749×10$^4$); (pH 6.9) 286 (1.143×10$^4$); (pH 13) 290 (0.914×10$^4$); $^1$H NMR δ5.49 (s, 2 H, ArCH$_2$), 7.36–7.54 (m, 5 H, ArH), 8.02 (s, 1 H, H-8 ), 11.8 (br s, 1 H, NH, exchanges with D$_2$O), 13.2 (br s, 1 H, NH, exchanges with D$_2$O); MS (EI) calcd. m/z for C$_{12}$H$_{10}$N$_4$O$_2$ 242.0803, found 242.0828; Anal. (C$_{12}$H$_{10}$N$_4$O$_2$ H$_2$O) C, H, N.

EXAMPLE 11

O$^6$-Benzyluric acid (4b)

Sodium nitrite (1.5 g, 43 mmol) dissolved in water (5 mL) was added to a suspension of O$^6$-benzyl-8-oxoguanine (1c) (0.257 g, 1.0 mmol) in acetone (5 mL). Glacial acetic acid (3 mL) was added to the suspension with stirring. After stirring for 3 h at room temperature a bright yellow precipitate formed. The suspension was mixed with water (150 mL) and undissolved solid was filtered off. Saturated aqueous sodium carbonate solution was added to the filtrate to adjust the pH to approximately 5. A yellow precipitate (130 mg) was collected and washed with water. This solid was crystallized from 50% aqueous ethanol to give an analytically pure sample of 4b: yield, 75 mg (29%); mp >230° C.; UV (pH 1) $\lambda_{max}$236 nm (sh) ($\epsilon$=0.972×10$^4$), 299 (1.427×10$^4$); (pH 6.9) 240 (sh) (0.821×10$^4$), 304 (2.134×10$^4$); (pH 13) 245 (sh) (0.846×10$^4$), 297 (1.861×10$^4$); $^1$H NMR δ5.43 (s, 2 H, ArCH$_2$), 7.35–7.51 (m, 5 H, ArH), 10.76 (s, 1 H, NH, exchanges with D$_2$O), 11.23 (s, 1 H, NH, exchanges with D$_2$O), 11.39 (s, 1 H, NH, exchanges with D$_2$O); MS (EI) calcd. m/z for C$_{12}$H$_{10}$ N$_4$ O$_3$258.0752, found 258.0753; Anal. (C$_{12}$H$_{10}$ N$_4$O$_3$.5/2 H$_2$O) C, H, N.

EXAMPLE 12

Diacetyl-O$^6$-benzyl-8-oxoguanine

Acetic anhydride (2 mL) was added to the suspension of O$^6$-benzyl-8-oxoguanine (1c) (0.257 g, 1.0 mmol) in dry toluene (10 mL). The suspension was vigorously refluxed for 24 hr, and was cooled to room temperature. After storing at 4° C. for 4 hr, the resulting precipitate was collected by filtration, washed with benzene and air dried to give an analytically pure sample of a diacetylated product: yield, 0.287 g (84%); mp 272–274° C. dec.; UV (100% MeOH) δ$_{max}$ 275 nm ($\epsilon$=1.313×10$^4$); (pH 1) 275 (1.143×10$^4$); (pH 6.9) 238 (0.995×10$^4$), 276 (1.115×10$^4$); (pH 13) 285 (2.138× 10$^4$); $^1$H NMR δ2.18 (s, 3 H CH$_3$), 257 (s, 3 H, CH$_3$), 5.51 (s, 2 H, ArCH$_2$), 7.30–7.57 (m, 5 H, ArH), 10.41 (s, 1 H, exchanges with D$_2$O), 12.30 (s, 1H, exchanges with D$_2$O); MS (EI) Calcd. m/z forC$_{16}$H$_{15}$N$_5$O$_4$: 341.1123. Found: 341.1130. Anal. (C$_{16}$H$_{15}$N$_5$O$_4$) C, N, H.

EXAMPLE 13

N$^2$-Acetyl-O$^6$-benzyl-8-oxoguanine (4d)

Diacetyl-O$^6$-benzyl-8-oxoguanine (85 mg, 0.25 mmol) was dissolved in methanol (10 mL) and ammonium hydroxide (28%, 5 mL) and was allowed stand for 1 hr. The clear solution became cloudy and a precipitate formed on standing. The precipitate was collectedby filtration, washed with water, and dried to give an analytically pure sample of 4d: yield, 48 mg (65%); mp 335–337° C. dec.; UV (pH 1) $\lambda_{max}$ 276 nm ($\epsilon$×1.723×10$^4$), 303 (sh) 0.679×10$^4$); (pH 6.9) 276 (1.379×10$^4$); (pH 13) 284 (1.683×10$^4$); $^1$H NMR δ 2.15 (s, 3 H, CH$_3$), 5.49 (s, 2H, ArCH$_2$), 730–7.55 (m, 5 H, ArH), 10.21 (s, 1 H, exchanges with D$_2$O), 10.99 (s, 1 H, exchanges with D$_2$O), 11.6 (s, 1 H, exchanges with D$_2$O; MS (EI) Calcd. m/z for C$_{14}$H$_{13}$N$_5$O$_3$:299.108. Found: 299.1023. Anal. (C$_{14}$H$_{13}$N$_5$O$_3$) C, N, H.

EXAMPLE 14

O$^6$-Benzyl-2-fluorohypoxanthine (4c)

O$^6$-Benzylguanine (1.21 g, 5 mmol) was added to 100 mL of 48% fluoboric acid at –20° C. Sodium nitrite (1.23 g, 35 mmole) was dissolved in water (5 mL) and 2.5 mL of this sodium nitrite solution was added slowly to the cold fluoboric acid solution. The resulting mixture was stirred for 1 h at or below –15° C. Additional fluoboric acid (25 mL) was added followed by an additional 2.5 mL of the aqueous sodium nitrite solution. After stirring for an additional 1 h below –15° C, fluoboric acid (25 mL) was again added and stirring was continued for 1 h. The resulting solution was neutralized with saturated aqueous sodium carbonate solution at –20° C. and was allowed to warm to room temperature. A white precipitate that formed was collected by filtration and was washed with water and dried under vacuum to afford crude 4c: yield, 0.52 g, 43%. An analytical sample was prepared by chromatography on a Sephadex LH-20 column (3×80 cm) eluted with methanol/water (1:1) at 1 mL/min. The desired 4 c eluted in fractions 66–77: mp 182–183° C. (184–185° C.; Robins and Robins, J. Org. Chem., 34, 2160–2163 (1969)); UV (pH 1) $\lambda_{max}$ 256 nm ($\lambda$×1.117×10$^4$); (pH 6.9) 257 (1.078×10$^4$); (pH 13) 264 (1.063×10$^4$); $^1$H NMR δ5.60 (s, 2 H, ArCH$_2$), 7.37–7.57 (m, 5 H, ArH), 8.40 (s, 1 H, H-8), 13.60 (s, 1 H, NH, exchanges with D$_2$O), $^{19}$F NMR δ23.54 downfield from trifluoroacetic acid standard; MS (EI) calcd. m/z for C$_{12}$H$_9$FN$_4$O 244.0760, found 244.0756; Anal. (C$_{12}$H$_9$FN$_4$O.⅔ H$_2$O) C, H, N.

EXAMPLE 15

O$^6$-Benzyl-N$^2$-methylguanine (4e)

Fluoboric acid (48%, 30 mL) was cooled to –20° C. in an dry ice-acetone bath. O$^6$-Benzylguanine (0.362 g, 1.5 mmol) was added with stirring. Sodium nitrite (0.369 g, 10.5 mmol) was dissolved in water (1 mL) and 0.5 mL of this solution was added slowly to the cold fluoboric acid solution. The resulting solution was stirred at or below –15° C. for 1 h. More fluoboric acid (5 mL) was then added followed by 0.5 mL of the sodium nitrite solution. After stirring for 1 h at or below –15° C., fluoboric acid (5 mL) was again added and stirring was continued for an additional 1 h. Methylamine (40% in water, 60 mL) was then added at –20° C., and the resulting basic solution was stirred at room temperature for 2 days. The solvent was evaporated under reduced pressure to produce a white solid. The solid was suspended in 50 mL of H$_2$O with stirring for 10 min. Undissolved material was collected by filtration and washed with water. This solid was dissolved in 40 mL methanol/water (1:1) to which was added 1.2 mL of 28% aqueous ammonia solution. The solution was loaded on a 3×80 cm Sephadex LH-20 column eluted with MeOH/H$_2$O/NH$_4$OH (30:70:3) at 1 mL/min. Column eluent was continuously monitored at 280 nm and fractions (10 mL) were collected. Evaporation of the pooled fractions 106–127 gave an analytically pure sample of 4e: yield, 85 mg (22%); mp 189–190° C.; UV (pH 1) $\lambda_{max}$ 238 nm (sh) ($\epsilon$=0.665×10$^4$), 297 (0.904×10$^4$); (pH 6.9) 246 (0.898×10$^4$), 290 (0.676×10$^4$); (pH 13) 240 (sh) (0.615×10$^4$), 294 (0.674×10$^4$); $^1$H NMR $\delta$ 2.30 (d, 3 H, CH$_3$), 5.50 (s, 2 H, ArCH$_2$), 6.75 (m, 1 H, MeNH, exchanges with D$_2$O), 7.31–7.53 (m, 5 H, ArH), 7.82 (s, 1 H, H-8), 12.53 (s, 1 H, NH, exchanges with D$_2$O); MS EI) calcd. m/z for C$_{13}$H$_{13}$N$_5$O 255.1120, found 255.1107: Anal. (C$_{13}$H$_{13}$N$_5$0.½ H$_2$O) C, H, N.

EXAMPLE 16

O$^6$-Benzyl-N$^2$, N$^2$-dimethylguanine (4f)

Fluoboric acid (48%, 40 mL) was cooled to –20° C. in an dry ice-acetone bath. O$^6$-Benzylguanine (0.482 g, 2.0 mmol) was added with stirring. Sodium nitrite (0.492 g, 14.0 mmol) was dissolved in water (2 mL) and 1 mL of this solution was added slowly to the cold fluoboric acid solution. The resulting solution was stirred at or below –15° C. for 1 h. More fluoboric acid (10 mL) was added followed by the addition of 1 mL of the sodium nitrite solution. After stirring for 1 h at or below –15° C., additional fluoboric acid (10 mL) was added with stirring for 1 h. Dimethylamine (40% in water, 60 mL) was then added to the solution at –20° C., and the resulting mixture was allowed to warm to room temperature. The suspension became a clear solution and a precipitate formed within 10 min. After standing overnight at room temperature the precipitate was collected by filtration and was washed with water. The solid was crystallized from 50% aqueous ethanol to give an analytically pure sample of 4f: yield, 0.25 g (46%); mp 220–221° C. dec.; UV (pH 1) $\lambda_{max}^{248}$ nm (sh) ($\epsilon$=0.512×10$^4$), 303 (0.908×10$^4$); (pH 6.9) 251 (1.152×10$^4$), 299 (0.686×10$^4$): (pH 13) 248 (sh) (0.766×10$^4$), 299 (0.710×10$^4$); $^1$H NMR $\delta$ 3.12 (s, 6 H, CH$_3$), 5.54 (s, 2 H, ArCH$_2$), 7.36–7.51 (m, 5 H, ArH), 7.84 (s, 1 H, H-8), 12.56 (s, 1 H, NH, exchanges with D$_2$O); MS (EI) calcd. m/z for C$_{14}$H$_{15}$N$_5$O 269.1276, found 269.1254; Anal. (C$_{14}$H$_{15}$N$_5$O) C, H, N.

EXAMPLE 17

2,4-Diamino-6-benzyloxy-5-bromopyrimidine (3f)

2,4-Diamino-5-bromo-6-chloropyrimidine ( Phillips et. al., *J. Org. Chem.*, 29, 1488–1490 (1963)) (2.3 g, 10 mmol) was added to a solution of sodium(0.29 g, 12.5 mmol) in benzyl alcohol ( 10 mL) under argon. The solution was heated in a 130° C. oil bath for 3 h and the benzyl alcohol was evaporated under reduced pressure to give a white solid. This solid was washed with water, and air dried. Crystallization from 50% aqueous ethanol gave white crystalline needles of 3f: yield, 2.32 g (76%); mp 165–166 ° C. (lit. 136° C.; Kosary et. al., *Acta Pharm. Hung.*, 49, 241–247 (1989)); UV (pH 1) $\lambda_{max}^{236}$ nm ($\epsilon$=0.873×10$^4$), 291 (1.388×10$^4$O); (pH 6.9) 236 (0.850×10$^4$), 277 (0.835×10$^4$); (pH 13) 234 (0.869×10$^4$), 277 (0.827×10$^4$ ); $^1$H NMR $\delta$ 5.30 (s, 2 H, ArCH$_2$), 6.15 (s, 2 H, NH$_2$, exchange with D$_2$O), 6.32 (s, 2 H, NH$_2$, exchange with D$_2$O), 7.31–7.45 (m, 5 H, ArH); MS (EI) calcd. m/z for C$_{11}$H$_{11}$N$_4$O$^{79}$Br 294.0115, found 294.0127; calcd. m/z for C$_{11}$H$_{11}$N$_4$O$^{81}$Br 296.0094, found 296.0083; Anal. (C$_{11}$H$_{11}$N$_4$OBr) C, H, N.

EXAMPLE 18

2-Amino-4-chloro-5-nitropyrimidine

A suspension of 1-amino-4-hydroxy-5-nitropyrimidine (5.0 g, 32.1 mmol) in phosphorous oxychloride (100 mL) was refluxed overnight, and the excess phosphorous oxychloride was evaporated under reduced pressure. The residue was mixed with ice (100 g) in an ice-bath, and the mixture was neutralized with concentrated aqueous sodium carbonate solution. A yellow precipitate was collected by filtration and washed with water: yield, 1.39 g (25%); mp 191–194° C. dec.; $^1$H NMR $\lambda$.8.45 (br s, 2 H, NH$_2$, exchange with D$_2$O), 9.03 (s, 1 H, H-6); MS (EI) calcd. m/z for C$_4$H$_3$N$_4$O$_2$$^{35}$Cl 173.9944, found 173.9934; calcd. m/z for C$_4$H$_3$N$_4$O$_2$$^{37}$Cl 175.9915, found 175.9916.

EXAMPLE 19

2-Amino-4-benzyloxy-5-nitropyrimidine (5a)

2-Amino-4-chloro-5-nitropyrimidine (0.70 g, 4.0 mmol) was added to a solution of sodium (0.12 g, 5.2 mmol) in benzyl alcohol (8 mL) under argon. The solution was heated in a 130° C. oil bath for 3 h, and approximately half of the benzyl alcohol was evaporated under reduced pressure. The residue was poured into water (50 mL) with constant stirring for 10 min. After neutralization with glacial acetic acid, a brown precipitate formed which was collected by filtration and washed with water. This solid was crystallized from benzene to give 5a as a golden crystalline solid: yield, 126 mg (13%); mp 164–167° C.; UV (pH 1) $\lambda_{max}$ 262 nm ($\epsilon$=0.879×10$^4$), 295 (sh) (0.571×10$^4$); (pH 6.9) 235 (sh) (0.448×10$^4$), 273 (0.360×10$^4$), 326 (1.085×10$^4$); (pH 13) 273 (0.404×10$^4$), 327 (1.055×10$^4$); $^1$H NMR $\delta$ 5.51 (s, 2 H, ArCH$_2$), 7.35–7.54 (m, 5 H, ArH), 8.05 (d, 2 H, NH$_2$, exchange with D$_2$O), 8.92 (s, 1 H, H-6); MS (EI) calcd. m/z for C$_{11}$H$_{10}$ N$_4$O$_3$ 246.0752, found 246.0758; Anal. (C$_{11}$H$_{10}$N$_4$O$_3$) C, H, N.

EXAMPLE 20

2-Amino-4-benzyloxy-6-methyl-5-nitropyrimidine (5b)

2-Amino-4-chloro-6-methyl-5-nitropyrimidine (Boon et al., *J. Chem. Soc.*, 96–102 (1951)) (1.24 g, 6.58 mmol) was added to a solution of sodium (0.21 g, 9.13 mmol) in benzyl alcohol (14 mL) under argon. The solution was heated in a 135° C. oil bath for 3.5 h, and was poured into water (70 mL) with constant stirring for 10 min. After neutralization with glacial acetic acid, a yellow precipitate formed which was collected by filtration and washed with water. This solid was crystallized from benzene to give 5b as a bright yellow crystalline solid: yield, 0.57 g (33%); mp 159–160° C.; UV (pH 1) $\lambda_{max}$ 268 nm ($\epsilon$=0.783×10$^4$), 345 (sh) (0.104×10$^4$); (pH 6.9) 282 (0.564×10$^4$), 345 (sh) (0.338×10$^4$); (pH 13) 282 (0.549×10$^4$), 345 (sh) (0.332×10$^4$); $^1$H NMR $\delta$ 2.35 (s, 3 H, CH$_3$), 5.44 (s, 2 H, ArCH$_2$), 7.34–7.46 (m, 5 H, ArH), 7.64 (b s, 2 H, NH$_2$, exchange with D$_2$O); MS (EI) calcd. m/z for C$_{12}$H$_{12}$N$_4$ 0$_3$260.0908, found 260.0913; Anal. (C$_{12}$H$_{12}$N$_4$O$_3$) C, H, N.

EXAMPLE 21

2,4-Diamino-6-benzyloxy-s-triazine (6)

2,4-Diamino-6-chloro-s-triazine (2.25 g, 15.0 mmol) was added to a solution of sodium (0.43 g, 18.8 mmol) in benzyl alcohol (30 mL) under argon. The suspension was heated in a 130° C. oil bath for 3.5 h. The excess benzyl alcohol was removed under vacuum and the resulting solid was collected with the aid of benzene, and washed with water (100 mL): yield, 1.83 g (56%); mp 184–185° C. (lit. 186–188° C.; Wakabayashi et al., Nippon Dojo-Hiryogaku Zasshi, 41, 193–200 (1970)); UV (pH 1) $\lambda_{max}$ 233 nm (sh) ($\epsilon$=0.589×

$10^4$); (pH 6.9) 238 (sh) (0.111×$10^4$): (pH 13) 240 (sh) (0.073×$10^4$); $^1$H NMR δ 5.25 (s, 2H, ArCH$_2$), 6.63 (s, 4 H, NH$_2$, exchange with D$_2$O), 7.30–7.42 (m, 5 H, ArH); MS (EI) calcd. m/z for $C_{10}H_{11}N_5O$ 217.0963, found 217.0955.

EXAMPLE 22

2-Amino-6-chloro-8-trifluoromethylpurine

A suspension of 8-trifluoromethylguanine (Pfleiderer and Shanshal, *Liebigs Ann. Chem.*, 726, 201–215 (1969)) (2.0 g, 9.1 mmol) in phosphorous oxychloride (20 mL) was refluxed for 3 h. Excess phosphorous oxychloride was evaporated under reduced pressure. The resulting residue was mixed with ice-water (100 g), and the pH was adjusted to 3–4 with a concentrated aqueous NaOH solution. The resulting solution was mixed with MeOH (100 mL) and approximately half (i.e., 100 mL) of the aqueous methanol solution was loaded on a 3×80 cm Sephadex LH-20 column eluted with methanol/water (1:1) at 1 mL/min. Column eluent was continuously monitored at 280 nm and fractions (10 mL) were collected. The remainder of the reaction mixture in MeOH/H$_2$O was chromatographed separately under identical conditions. The desired product eluted in fractions 73–85. Evaporation of solvent from the pooled fractions 73–85 from both chromatographic runs afforded analytically pure 2-amino-6-chloro-8-trifluoromethylpurine: yield,0.94 g (43%); mp >225° C. dec.; UV (pH 1) $\lambda_{max}$ 245 nm (ε=0.501×$10^4$), 314 (0.746××$10^4$); (pH 6.9) 270 (0.265 ×$10^4$), 315 (0.612×$10^4$); (pH 13) 272 (0.269×$10^4$ ), 314 (0.612×$10^4$); $^1$H NMR δ 7.19 (s, 2 H, NH$_2$, exchange with D$_2$O), 14.25 (br s, 1 H, NH, exchanges with D$_2$O); MS (EI) calcd. m/z for $C_6H_3$ $N_5F_3{}^{35}Cl$ 237.0029, found 237.0011; calcd. m/z for $C_6H_3N_5F_3{}^{37}Cl$ 239.0000, found 238.9987; Anal. ($C_6H_3N_5F_3C$) C, H, N, F, Cl.

EXAMPLE 23

$O^6$-Benzyl-8-trifluoromethylguanine (1e)

Sodium (0.10 g, 4.3 mmol) was stirred in 5 mL of benzyl alcohol until all had reacted. 2-Amino-6-chloro-8-trifluoromethylpurine (0.475 g, 2.0 mmol) was added, and the reaction mixture was heated in a 135° C. oil bath for 3.5 h. The benzyl alcohol was removed by vacuum distillation yielding a brown oil. The oil was dissolved in water (50 mL) and was acidified with glacial acetic acid to produce a pale yellow precipitate. The precipitate was collected by filtration and washed with water. The crude product was loaded on a 2.5×35 cm silica gel column (Davisil grade 633, 200–425 mesh, 60 Å). Elution was carried out with 5% EtOH in CHCl$_3$ to provide analytically pure $O^6$-benzyl-8-trifluoromethylguanine (1e): yield, 0.42 g (67%); mp 214–216° C. dec.; UV (pH 1) $\lambda_{max}$ 291 nm (ε=1.229×$10^4$); (pH 6.9) 244 (0.470×$10^4$ ), 289 (1.023×$10^4$); (pH 13) 247 (sh) (0.393×$10^4$), 290 (0.923×$10^4$); $^1$H NMR δ5.51 (s, 2 H, ArCH$_2$), 6.82 (s, 2 H, NH$_2$, exchange with D$_2$O), 7.38–7.55 (m, 5 H, ArH), 13.75 (br s, 1 H, NH, exchanges with D$_2$O); MS (EI) calcd. m/z for $C_{13}H_{10}$ $N_5OF_3$ 309.0837, found 309.0827; Anal. ($C_{13}H_{10}N_5$ $OF_3$) C, H, N, F.

EXAMPLE 24

$O^6$-Benzyl-8-trifuloromethyl-9-methylguanine (7)

To $O^6$-benzyl-8-trifluoromethylguanine (1e) (200 mg, 0.65 mmol) under argon was added 0.66 mL of a 1.0 M solution of sodium ethoxide in ethanol. The solution was stirred for 10 min and the ethanol was removed under vacuum. The remaining solid was dissolved in anhydrous DMF (1.5 mL), and methyl iodide (49 µL, 0.78 mmol) was added to the solution. This solution was stirred at room temperature for 1 h, and 1.5 mL additional DMF was added. The solution was stirred at room temperature overnight. The solvent was evaporated under reduced pressure. The crude solid was loaded on a 2.5×35 cm silica gel column (Davisil grade 633, 200–425 mesh, 60 Å). Elution was carried out with chloroform/hexane (3:1) to provide analytically pure $O^6$-benzyl-8-trifluoromethyl-9-methylguanine (7): yield, 95 mg (45%); mp 86–89° C.; UV (pH 1) $\lambda_{max}$ 244 nm (ε=0.581×$10^4$), 286 (1.274×$10^4$); (pH 6.9) 252 (0.608×$10^4$), 288 (1.022×$10^4$); (pH 13) 252 (0.618×$10^4$), 288 (1.038× $10^4$); $^1$H NMR δ3.70 (s, 3 H, CH$_3$), 5.51 (s, 2 H, ArCH$_2$), 6.91 (s, 2 H, NH$_2$, exchange with D$_2$O), 7.38–7.54 (m, 5 H, ArH); MS (EI) calcd. m/z for $C_{14}H_{12}N_5OF_3$ 323.0994, found 323.0978; Anal. ($C_{14}H_{12}N_5OF_3$) C, H, N, F.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A pharmaceutical composition comprising a pharmaceutically acceptable carrier and a compound of the formula

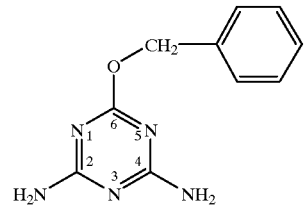

wherein said pharmaceutically acceptable carrier comprises polyethylene glycol 400 .

2. A method of enhancing the chemotherapeutic treatment of tumor cells in a mammal with an antineoplastic alkylating agent that causes cytotoxic lesions at the $O^6$-position of guanine, which method comprises:

administering to a mammal an effective amount of a compound of the formula

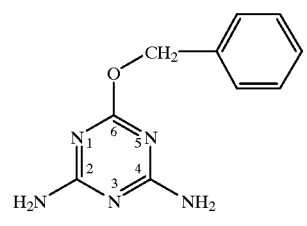

and administering to said mammal an effective amount of an antineoplastic alkylating agent which causes cytotoxic lesions at the $O^6$-position of guanine.

3. A method of inhibiting the reaction of $O^6$-alkylguanine-DNA-alkyltransferase with an alkylated DNA comprising reacting the $O^6$-alkylguanine-DNA-alkyltransferase with 2,4-diamino-6-benzyloxy-s-triazine.

* * * * *

UNITED STATES PATENT AND TRADEMARK OFFICE
CERTIFICATE OF CORRECTION

| | |
|---|---|
| PATENT NO. | : 6,303,604 B1 |
| APPLICATION NO. | : 09/590187 |
| DATED | : October 16, 2001 |
| INVENTOR(S) | : Moschel et al. |

It is certified that error appears in the above-identified patent and that said Letters Patent is hereby corrected as shown below:

At column 1, line 10 immediately before "TECHNICAL FIELD OF THE INVENTION," please add the following statement:

-- STATEMENT REGARDING
FEDERALLY SPONSORED RESEARCH AND DEVELOPMENT

This invention was also made with Government support under Grant Number CA18137 and CA47728 awarded by the National Cancer Institute of the National Institutes of Health. The Government has certain rights in this invention. --

Signed and Sealed this

Twentieth Day of February, 2007

JON W. DUDAS
*Director of the United States Patent and Trademark Office*